United States Patent [19]

Heilman et al.

[11] Patent Number: 5,098,369
[45] Date of Patent: Mar. 24, 1992

[54] BIOCOMPATIBLE VENTRICULAR ASSIST AND ARRHYTHMIA CONTROL DEVICE INCLUDING CARDIAC COMPRESSION PAD AND COMPRESSION ASSEMBLY

[75] Inventors: Marlin S. Heilman, Sarver; Steve A. Kolenik, Leechburg; Christopher D. Capone, Oakmont; Carl M. Parisi, Kittanning; Edward K. Prem, Allison Park; Vernon L. Speicher, Leechburg, all of Pa.

[73] Assignee: Vascor, Inc., Pittsburgh, Pa.

[21] Appl. No.: 522,956

[22] Filed: May 14, 1990

Related U.S. Application Data

[63] Continuation-in-part of Ser. No. 19,701, Feb. 27, 1987, Pat. No. 4,925,443.

[51] Int. Cl.⁵ .............................. A61N 1/362
[52] U.S. Cl. ............................ 600/16; 600/17; 128/419 D
[58] Field of Search ............ 600/15, 16, 17; 623/3; 128/419 D, 30.2

[56] References Cited

U.S. PATENT DOCUMENTS

| | | | |
|---|---|---|---|
| 4,192,293 | 3/1980 | Asrican | 600/17 |
| 4,536,893 | 8/1985 | Parravicini | 623/3 |
| 4,928,674 | 5/1990 | Halperin et al. | 128/419 D |
| 4,957,477 | 9/1990 | Lundbäck | 600/16 |

*Primary Examiner*—Francis Jaworski
*Assistant Examiner*—George Manuel
*Attorney, Agent, or Firm*—Fleit, Jacobson, Cohn, Price, Holman & Stern

[57] ABSTRACT

A ventricular assist device may include a cardiac compression assembly which comprises a gel-filled pad of generally concave configuration, mounted on a pressure plate with peripheral portions of the pad extending beyond the periphery of the plate, to preclude damage to the heart by the peripheral edges of the plate. The gel-filled pad may have undulating opposite sides formed by intersecting rows of raised dimples. The pad also includes portions for suturing the pad to a heart ventricle, and at least some of the dimples on the side of the pad facing the heart ventricle are provided with ventricle tissue growth-promoting islands. An electrode, in the form of a grid having intersecting strips which define dimple-receiving openings therebetween, also may be mounted on the venticle side of the pad. As many as eight circumferentially arranged cardiac compression assemblies, having lower ends pivotally mounted on a support member adapted to be located adjacent the apex of a heart ventricle, may be provided. Operating systems for operating the cardiac compression assemblies may include a motor-driven camming mechanism; a mechanism comprising a device for converting electrical energy to hydraulic fluid energy, two sealed fluid systems, a reversible pump, two bellows and a safety solenoid pump-bypass fluid return valve; or a closed loop system comprising a reversible pump in a fluid supply casing, a hydraulic fluid manifold including a plurality of miniature fluid actuators which may be of arcuate construction to conserve space, and a mechanism for collecting fluid leaking from the actuators and returning it to the fluid supply casing.

103 Claims, 11 Drawing Sheets

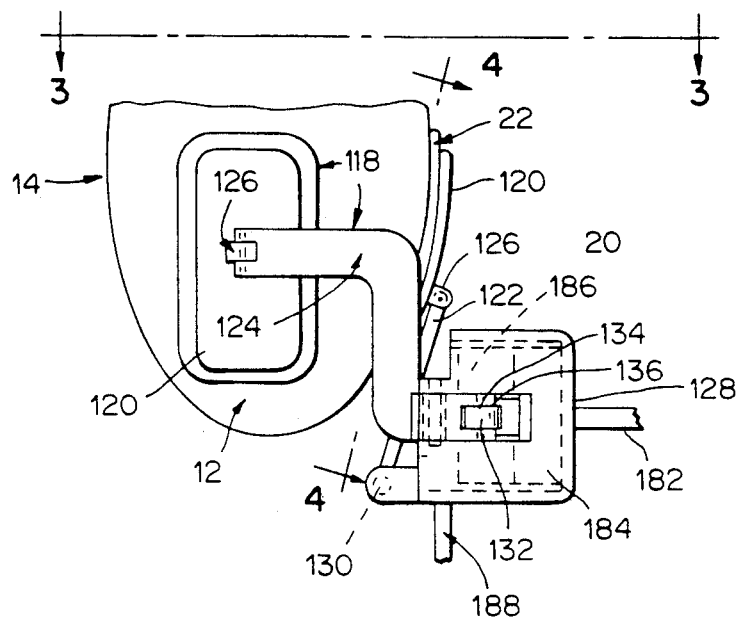
FIG. 1
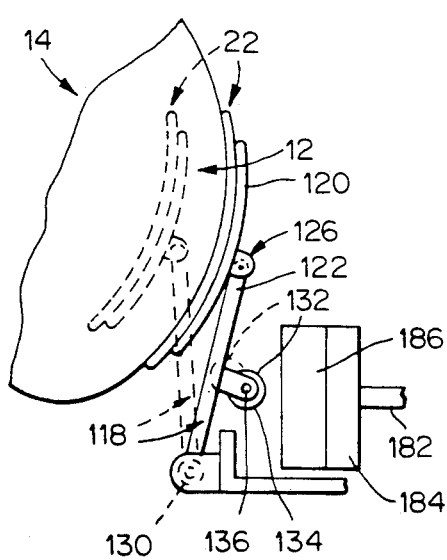
FIG. 2
FIG. 3

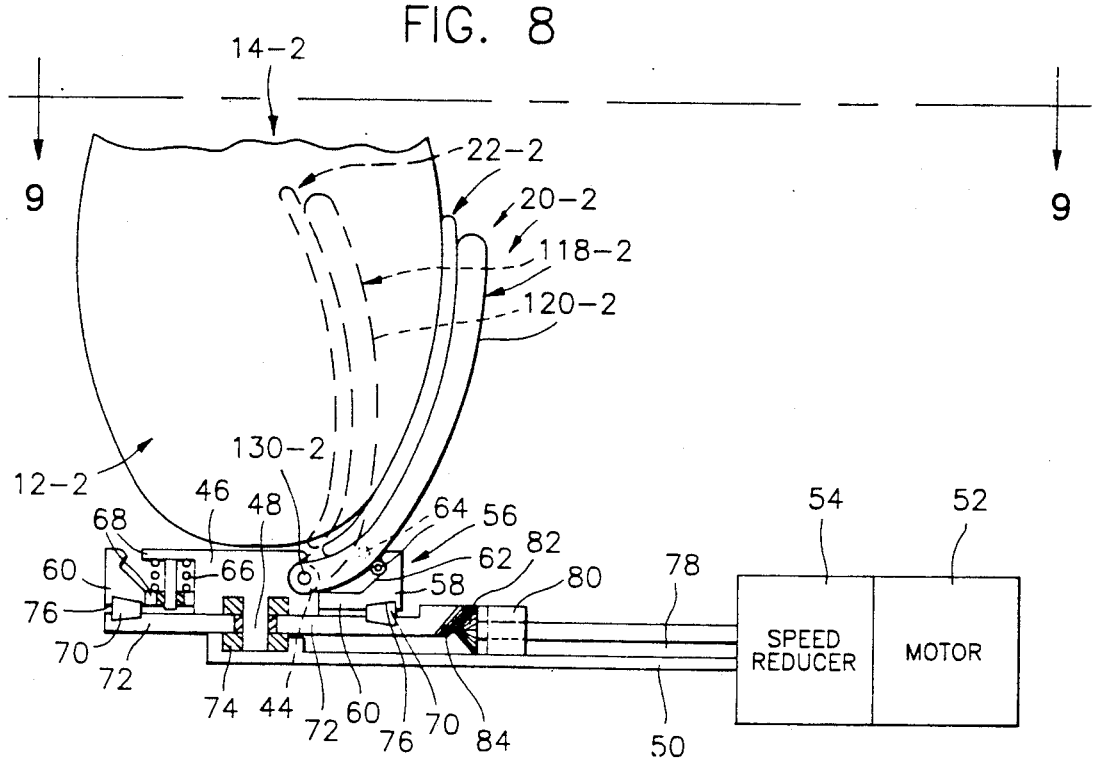
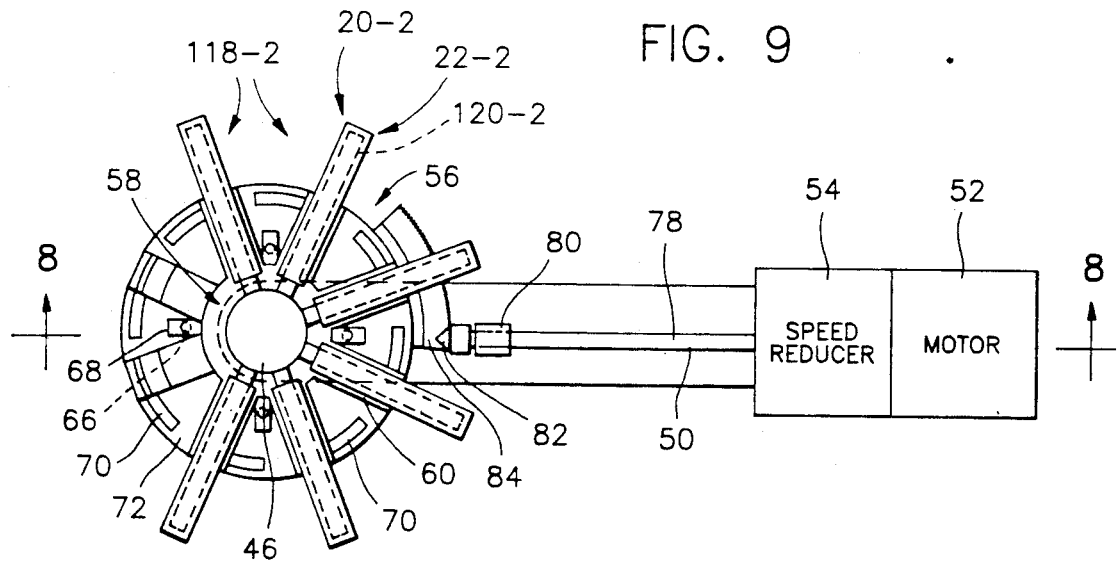

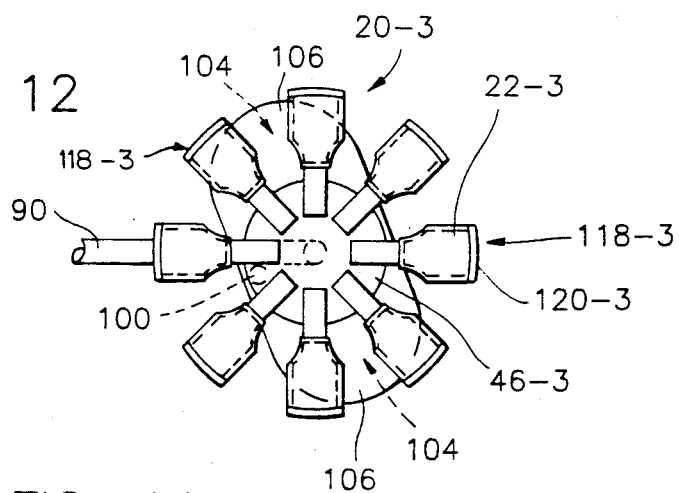
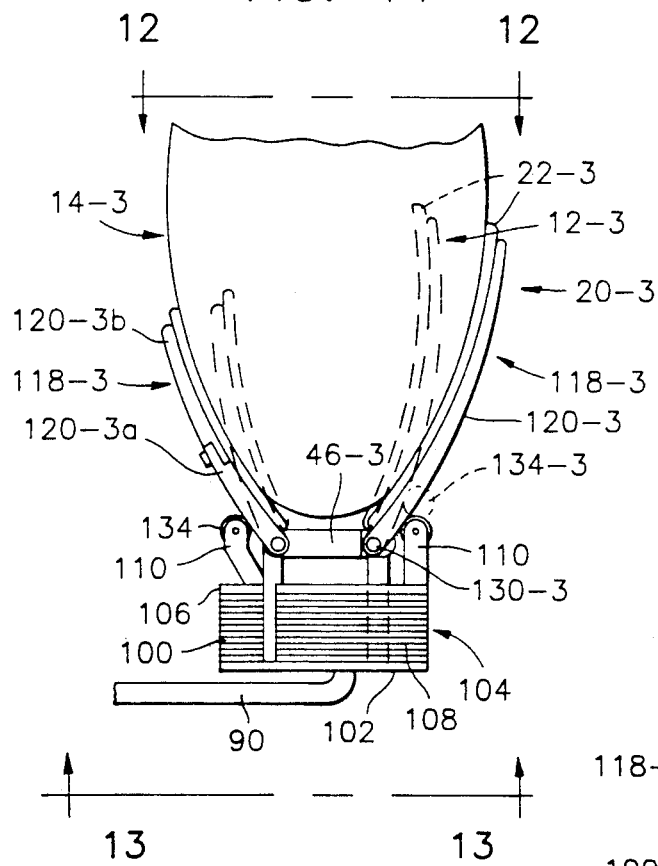
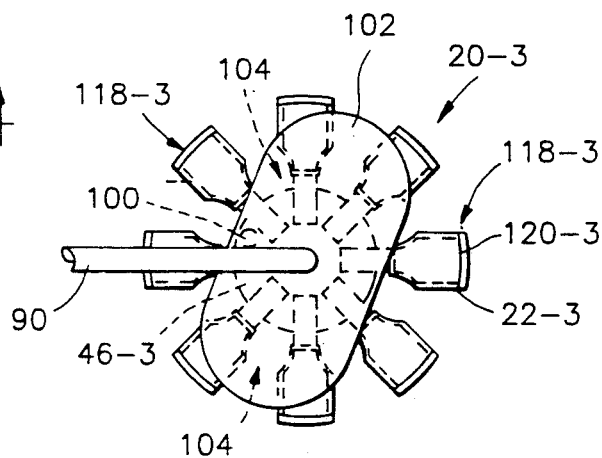

(DURING SYSTOLE)

(AFTER SYSTOLE)

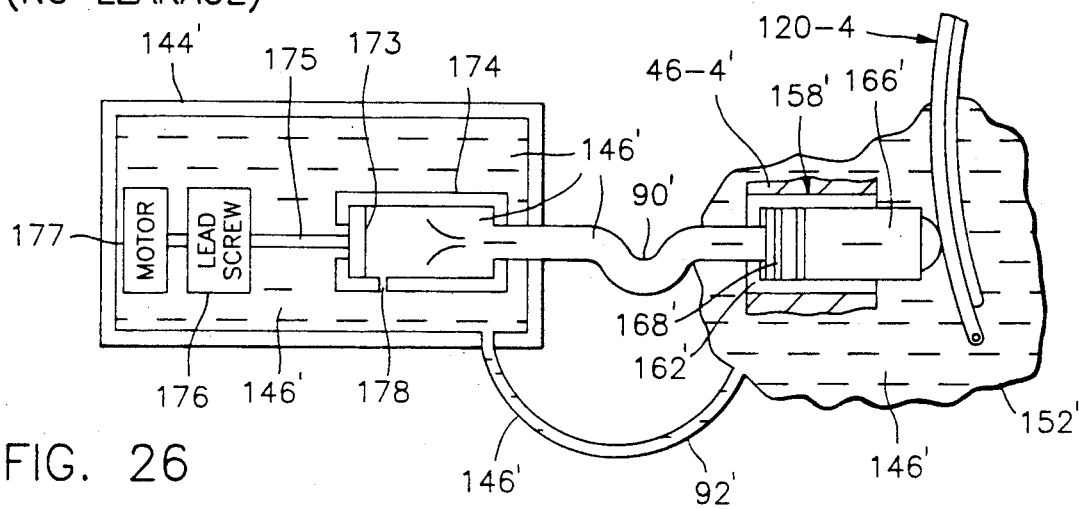
FIG. 25 (NO LEAKAGE)
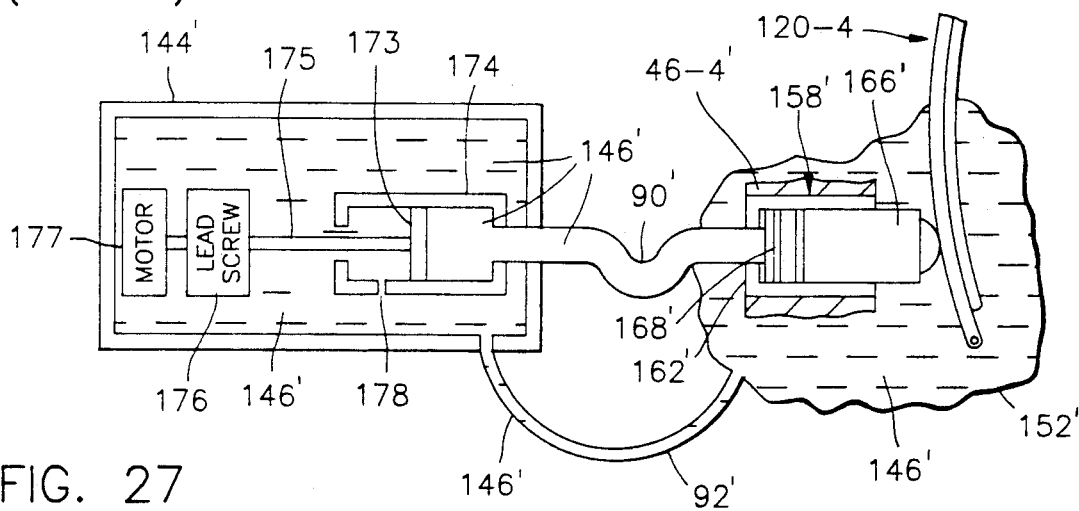
FIG. 26 (LEAKAGE)
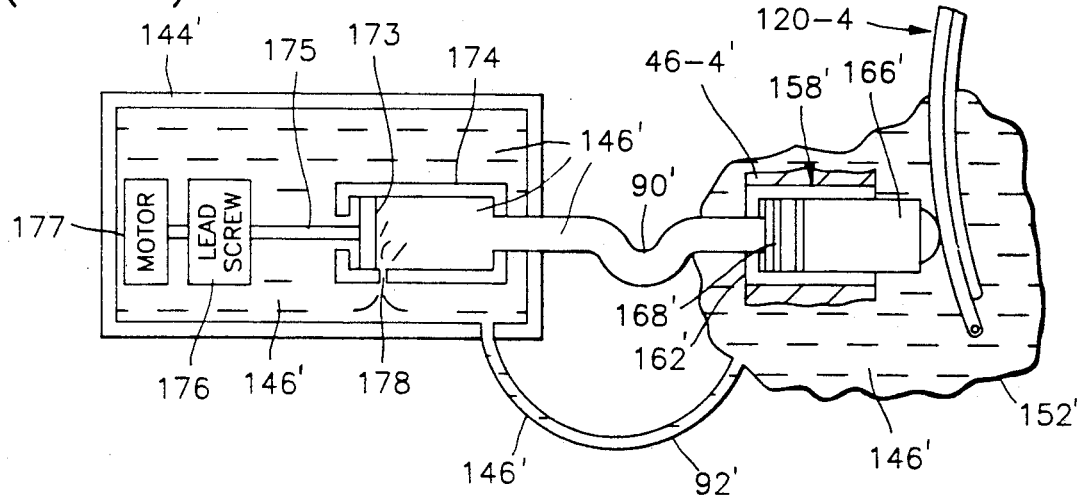
FIG. 27 (LEAKAGE)

BIOCOMPATIBLE VENTRICULAR ASSIST AND ARRHYTHMIA CONTROL DEVICE INCLUDING CARDIAC COMPRESSION PAD AND COMPRESSION ASSEMBLY

This is a continuation-in-part of application Ser. No. 07/019,701, filed Feb. 27, 1987, now U.S. Pat. No. 4,925,443.

BACKGROUND OF THE INVENTION

1. Field of the Invention

This invention relates to improvements in a biocompatible ventricular assist and arrhythmia control device, as disclosed in U.S. patent application Ser. No. 07/019,701, now U.S. Pat. No. 4,925,443, and more particularly to a biocompatible ventricular assist and arrythmia control device comprising a gel-filled contact pad which forms part of a cardiac ventricular compression assembly, for compressing a heart ventricle without damaging the ventricle.

2. Description of the Prior Art

U.S patent application Ser. No. 07/019,701, filed Feb. 27, 1987, in the names of Marlin S. Heilman and Steve A. Kolenik, entitled "Biocompatible Ventricular Assist and Arrythmia Control Device", and assigned to the same Assignee as the subject application, discloses an implantable ventricular, assist device which includes (1) one or more movable compression assemblies for engaging the left ventricle of the heart; (2) an operating mechanism for cyclically actuating the movable compression assemblies and thereby alternately ejecting blood from the ventricle and permitting the ventricle to refill; (3) a sensing means to detect adequacy of left ventricular stroke volume and/or pressure; (4) a control mechanism to assure adequate left ventricular stroke volume by regulating the compressive force of the compression assemblies, and also to control pacemaker, cardioverter/defibrillator, and recorder subsystems; and (5) an electrical power source.

Each compression assembly includes a contoured pressure plate and a soft contact pad mounted on the interior plate surface for suturing and/or gluing the compression assembly to the ventricle. To minimize mechanical stress on the myocardial surface, including the coronary arteries, the contact pad consists of an elastomer, such as silicone rubber, or a thermoplastic material (Shore A durometer range 30-50). To avoid edge stress, the thickness of each contact pad is progressively reduced toward its periphery. To further reduce stresses on the myocardium, bearings and axles are used to mount the pressure plates on the compression assembly's driving arm; if the contracting heart produces a torquing force, the joint will permit the pressure plate, within specified limits, to follow the natural movement of the heart.

However, while the above ventricular assist device is considered to represent a significant advance over the prior art, it has been found that the edges of the compression assembly pressure plates tend to create pressure points which may cause possible damage to the heart, and that the amount of the heart encompassed by the compression assemblies may not be sufficient in all instances. Accordingly, one purpose of this invention is to improve the operation of the compression assembly and preclude any such damage, by replacing the contact pad of each compression assembly with a gel-filled contact pad of novel and advantageous construction, which can compress the heart ventricle uniformly without damaging the ventricle. Another purpose of the invention is to provide a ventricular assist device and associated compression assemblies which encompass a greater portion of the heart, and which also overcome the disadvantages of other known cardiac ventricular assist devices, such as those of the expandable and contractible balloon type, which tend to have a short operating life because of the excessive cyclical stretching required in their operation.

SUMMARY OF THE INVENTION

In general, this invention relates to a cardiac compression pad of novel construction which is intended for use in a cardiac ventricular assist device, wherein the pad is mounted on a pressure plate of a cardiac ventricular compression assembly and adapted for engaging an outer surface of at least one heart ventricle, for compressing of the ventricle without damaging the ventricle.

More specifically, preferably the pad is gel-filled, has a generally concave configuration so as to be adapted to conform to the heart ventricle, and has an outer periphery which extends beyond an outer periphery of the pressure plate, to preclude damage to the ventricle by peripheral edges of the plate. The gel-filled pad includes a hollow sheath formed of soft, electrically insulating material having a specific gravity and stiffness similar to that of human muscle tissue, such as a polyurethane elastomer, so as to be adapted to be easily deformed. The hollow sheath, which is adapted for gluing and/or suturing of the cardiac compression assembly to the heart ventricle, may have undulating surfaces on opposite sides thereof, preferably formed by raised dimples, and is filled with a soft gel having the characteristics of polyurethane or silicon. An electrode for transmitting signals from the heart ventricle, and/or applying signals, such as cardioverting/defibrillating pulses, to the heart ventricle, may be mounted on a ventricle-engaging side of the sheath, in depressed portions of the associated undulating surface between the raised dimples. The electrode may be formed of a titanium wire mesh in the shape of a grid formed by intersecting strips which define dimple-receiving openings therebetween. Island-type surface portions, adapted to promote ventricle tissue growth to the gel-filled pad, and formed, for example, of DACRON (polyester), also may be provided on selected ones of the raised dimples on the ventricle-engaging side of the sheath. In the alternative, the ventricle-engaging side of the sheath may be provided with a protective porous foam material which also promotes tissue growth.

The invention also may include a circumferential arrangement of the cardiac compression assemblies which have lower ends pivotally mounted on a support member adapted to be located adjacent the apex of a heart ventricle with the cardiac compression assemblies essentially encircling a portion of the heart. The compression assemblies are pivoted to compress the heart by an operating mechanism, such as a motor-driven camming mechanism, or a mechanism comprising a device for converting electrical energy to hydraulic fluid energy, two sealed fluid systems, two spring bellows and a safety solenoid valve, or a mechanism comprising a hydraulic fluid manifold connected to plurality of miniature operating cylinders which may be of arcuate construction to conserve space.

An object of the invention is to provide a cardiac compression pad which precludes damage to a heart ventricle.

Another object of the invention is to provide a cardiac compression pad which is readily adapted for being secured to both a pressure plate of a cardiac compression assembly and a heart ventricle.

A further object of the invention is to provide a cardiac compression pad which is adapted to be easily deformed in response to movement of a heart ventricle.

An additional object of the invention is to provide a cardiac compression pad which is adapted to engage a heart ventricle so as to readily shrink and expand with the ventricle.

Another object of the invention is to provide a cardiac compression pad which facilitates transmitting signals from and/or applying signals to a heart ventricle.

A further object of the invention is to provide a cardiac compression pad which promotes heart ventricle tissue growth to the pad.

Another object of the invention is to provide an arrangement of cardiac compression assemblies which are adapted to substantially encircle a portion of a heart with respect to an apex of a heart ventricle.

BRIEF DESCRIPTION OF THE DRAWINGS

FIG. 1 is a front elevational view of a first embodiment of a direct cardiac pumping mechanism provided with gel-filled contact pads in accordance with the invention;

FIG. 2 is a separate front view of a part of the pumping mechanism shown in FIG. 1, illustrating first and second operating positions;

FIG. 3 is a top view as seen along the line 3—3 in FIG. 1;

FIG. 8 is a front elevational, cross-sectional view of a second embodiment of a direct cardiac pumping mechanism in accordance with the invention, with certain parts omitted, taken essentially along the line 8—8 in FIG. 9;

FIG. 9 is a top view as seen along the line 9—9 in FIG. 8;

FIG. 11 is a front elevational view, with certain parts omitted, of the pumping mechanism shown in FIG. 10;

FIG. 12 is a top view as seen along the line 12—12 in FIG. 11;

FIG. 13 is a bottom view as seen along the line 13—13 in FIG. 11;

FIG. 22-27 are schematic views illustrating the structure and operation of the fluid recovery system shown in FIG. 21.

DETAILED DESCRIPTION

Figure 4:
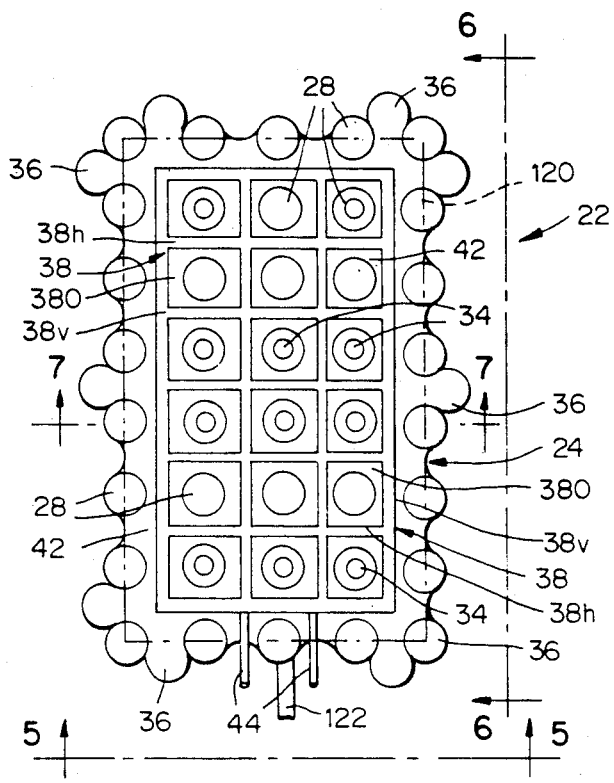
FIG. 4 is an enlarged elevational view of a gel-filled contact pad in accordance with the invention, as viewed along the line 4—4 in FIG. 1.

FIGS. 1-3 illustrate a left ventricle 12 of a heart 14 in conjunction with a direct cardiac pumping or compression mechanism 20 of a type disclosed in FIGS. 4a, b and c of U.S. patent application Ser. No. 07/019,701, filed Feb. 27, 1987, in the names of Marlin S. Heilman and Steve A. Kolenik, entitled "Biocompatible Ventricular Assist and Arrhythmia Control Device", and assigned to the same Assignee as the subject application, with like parts in FIGS. 1-3 being identified by the same reference numbers as in that application. The direct cardiac pumping mechanism 20 comprises a part of an implantable subsystem of a biocompatible ventricular assist and arrhythmia control device 10, the remainder of which is not shown, but which is described in detail in the aforementioned patent application, the disclosure of which, to the extent not inconsistent with this disclosure, is hereby incorporated by reference. The direct cardiac pumping mechanism 20 differs from the corresponding mechanism in the aforementioned patent application in being provided with a plurality of gel-filled contact pads 22 on pressure plates 120, for directly engaging the heart ventricle 12 in a uniform manner, so as to prevent damage to the ventricle, particularly at the edges of the pressure plates, and for other purposes, as is subsequently described herein.

Considering first the construction of the direct cardiac pumping mechanism 20 as disclosed in FIGS. 1-3, the pumping mechanism includes triaxial lateral pressure plate or compression assemblies 118 for engaging and compressing the heart left ventricle 12 in synchronism with native or pacemaker-initiated pumping action, or asynchronously during ventricle fibrillation. Each pressure plate assembly 118 includes one of the pressure plates 120, each of which is formed of a spring-tempered, biocompatible, inert metal, such as the nickel alloy MP35NR (an alloy of nickel, cobalt, chromium, and molybdenum). Each pressure plate 120 is attached to a driver arm 122 or 124 by way of an axle/bearing mount 126 so that the pressure plate may follow, within specified limits, an actual movement of the heart. Each driver arm 122 or 124 is mounted on an actuator housing 128 (FIGS. 1 and 3), being pivoted on a lightweight, high-performance bearing 130, which, like the bearing in the axial/bearing mount 126, may consist of a tubular lining of woven TEFLON (polytetraflouroethylene)/DACRON (polyester) fabric and an inner wound fiberglass epoxy resin matrix. The driver arms 122 and 124 and the actuator housing 128 each is formed of a biocompatible metal compound, such as Ti6A14V (titanium, aluminum, and vanadium). Driver arms 122 and 124 are engaged by wedge followers 132, each of which includes a roller 134 mounted on a follower bearing 136 (of similar construction to arm bearing 130).

The above pumping or compression mechanism 20 is readily adapted to varying combinations of pressure plate assemblies 118. For example, triaxial lateral placement could be supplemented with a fourth, smaller plate (not shown) positioned on the heart right ventricle (not shown), or with an apical plate (not shown) for supporting and supplying compressive force to the apex of the left heart ventricle 12. It should also be perceived that other embodiments of the pumping mechanism 20 are possible, and that the number of pressure plates 120, their positions on the heart, and the manner of operation of the pressure plate assemblies 118, can be modified. In this connection, the pressure plates can be made larger (e.g., wider) and their number reduced, or made smaller (e.g., thinner) and their number increased, as shown in FIGS. 8-20. Additional pumping mechanism arrangements are disclosed in the aforementioned U.S patent application Ser. No. 07/019,701.

The pressure plate assemblies 118 are movable between solid line positions, as shown in FIGS. 1-3, when the left ventricle 12 expands (diastole), and broken line positions (FIGS. 2 and 3) when the left ventricle contracts (systole). Operation of the pressure plate assemblies 118 to compress the left ventricle 12 is accomplished by a biocompatible fluid, such as mineral oil, flowing through a connection tube 182 from a rotary-to-axial drive-converting mechanism (not shown), as disclosed in the abovementioned U.S. patent application Ser. No. 07/019,701, into a bellows 184 in the actuator housing 128, to cause expansion of the bellows, to which is welded a driving wedge 186. In turn, the wedge 186 exerts lateral pressure on the wedge followers 132, which then cause the pressure plate assemblies 118 to pivot on the arm bearings 130 and compress the left ventricle 12 simultaneously.

Referring to FIGS. 4-7, since each of the gel-filled contact pads 22 is identical, only one will be described. As is shown in FIGS. 1-3, 5, 6 and 7, the gel-filled contact pad 22 has a generally concave configuration so as to be adapted to conform uniformly to the surface of the left ventricle 12, so that applied force by the pad is distributed uniformly over the ventricle's surface. The periphery of the gel-filled contact pad 22 also extends outward beyond the periphery of the associated pressure plate 120, to preclude damage to the left ventricle by pressure exerted from the peripheral edges of the plate, including damaging cardiac muscle or the coronary arteries, or interfering with the muscle's blood supply.

The gel-filled contact pad 22 includes a molded hollow sheath or body member 24 formed of a soft, electrically insulating material having a specific gravity and stiffness similar to that of human muscle tissue (i.e., the left ventricle 12), such as a polyurethane elastomer, so as to be adapted to be easily deformed, thereby reducing the possibility of pressure points occurring on the ventricle's surface, and preventing localized cardiac tissue damage. Further, the sheath 24, and thus the pad 22, preferably is filled with a soft gel 26 (FIG. 7), such as a polyurethane or silicon gel. The sheath 24 also preferably has a relatively thin wall thickness in a range on the order of 5-13 mils.

In the disclosed embodiment of the invention, the sheath 24 of the gel-filled contact pad 22 also has opposite sides each having an undulating surface formed by intersecting rows of three dimensional, curvilinear surfaces, in the form of raised dimples 28 molded into the pad surface and having a height in a range on the order of 32 mils, so that each side of the pad has a dimpled or pebbled configuration. The raised dimples 28 facilitate shrinkage and expansion of the surface of the gel-filled contact pad 22 with the left ventricle 12 in three dimensions as it expands and contracts in its operation. This allows the surface of the left ventricle 12 to shrink and expand naturally, without undue strain. The dimples 28 also offer a secondary benefit in that they reduce the stress level in the outer layer of the gel-filled contact pad 22.

Figure 6:
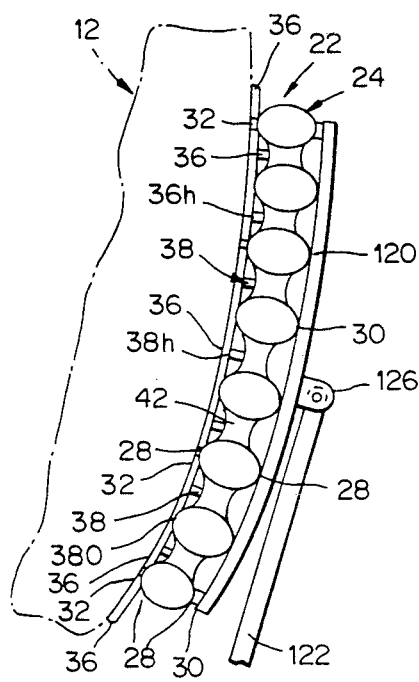
FIG. 6 is a side view as seen along the line 6—6 in FIG. 4.
Figure 5:
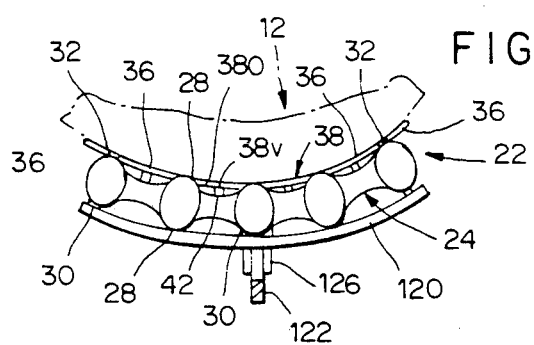
FIG. 5 is an end view as seen along the line 5—5 in FIG. 4.

Referring to FIGS. 5 and 6, selected ones of the raised dimples 28 on the side of the gel-filled contact pad sheath 24 facing its associated pressure plate 120, may be bonded or glued to the plate by an adhesive 30 consisting of an electrically insulating material, such as a silicone rubber or a thermoplastic, while other ones of the dimples may be left unbonded to permit flexibility of movement of the sheath 24 relative to the pressure plate in response to expansion and contraction of the left ventricle 12. Similarly, the tops of selected ones of the dimples 28 on the opposite side of the sheath 24 engaging the left ventricle 12, may be bonded or glued to the ventricle by a similar adhesive 32. Other selected ones of the raised dimples 28 on the ventricle-engaging side of the sheath 24 may be provided with small islands 34 (FIGS. 4 and 7) of a material, such as DACRON (polyester), for promoting tissue growth between the gel-filled contact pad 22 and the left ventricle 12. The gel-filled contact pad 22 also may be sutured to the left ventricle 12, as for example, by projecting tabs 36 integrally molded with the sheath 24, for example, to selected ones of the dimples 28 at opposite edges of the sheath, as illustrated in FIGS. 4-7. Thus, the tissue growth-producing islands 34, adhesive 32 and the suturing tabs 36 cooperate to firmly anchor the gel-filled contact pad 22 to the left ventricle 12.

Figure 7:
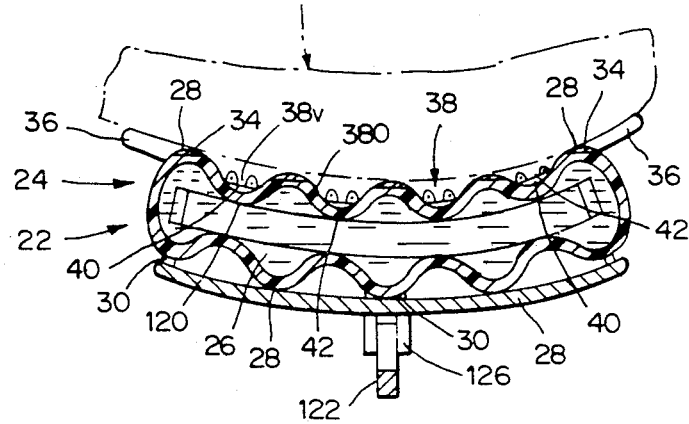
FIG. 7 is a further enlarged cross-sectional view, as seen along the line 7—7 in FIG. 4.

The gel-filled contact pad 22 also includes an electrode 38 (best shown in FIGS. 4 and 7) for transmitting heart signals from the left ventricle 12, and/or for applying control signals, such as cardioverting/defibrillating pulses, to the ventricle. In the disclosed embodiment of the invention, the electrode 38 is in the form of a rectangular grid formed, for example, of a titanium wire mesh and including, as viewed in FIG. 4, intersecting horizontal strips 38h and vertical strips 38v, which define dimple-receiving openings 38o (FIG. 4) therebetween. The strips 38h and 38v are bonded, such as by adhesive 40 (shown only in FIG. 7), in depressed portions or "valleys" 42 of the undulating surface of the gel-filled contact pad sheath 24 facing the left ventricle 12, between the raised dimples 28 of the undulating surface, as shown in FIGS. 4-7, with the dimples received in the openings 38o. The thickness of the mesh forming the electrode 38 is slightly less than the height of the raised dimples 28, (e.g., 20 mils) such that when the gel-filled contact pad 22 is engaged with the left ventricle 12, as illustrated in FIGS. 5, 6 and 7, the dimples can compress slightly, with the electrode wire mesh coming into direct engagement with the ventricle. The electrode 38 is connected to a control unit (not shown), which includes a cardioverter/defibrillator unit, as disclosed in the abovementioned U.S. patent application Ser. No. 07/019,701, by suitable electrical conductors 44 (shown only in FIG. 4) extending from one end of the electrode to an electrical conductor conduit or cable 188 (FIG. 1) bonded to the actuator housing 28.

In addition to the advantages described above, the gel-filled contact pads 22 also are advantageous in that they can be placed over bypass grafts with no significant deleterious reduction in blood flow in the grafts, because of the soft nature of the pads and because pumping assistance force to the left ventricle 12 is only applied during cardiac systole when coronary blood flow is minimal. In this connection, most coronary blood flow occurs during cardiac diastole when the gel-filled contact pads 22 are not applying force to the surface of the left ventricle 12.

Referring to FIGS. 8 and 9, the second embodiment of the invention shown comprises a pumping or compression mechanism 20-2 which includes six pressure plate or compression assemblies 118-2 (all shown only in FIG. 9) each having an elongated pressure plate or finger 120-2 provided with a gel-filled compression pad 22-2, which may be of the same construction as shown in FIGS. 4-7, for applying pressure to a left ventricle 12-2 of a heart 14-2. A forked lower end of each pressure plate 120-2 is pivotally mounted on a lug portion 44 of a central support member, such as a hub 46, by a pivot pin 130-2. The support hub 46 includes a depending central shaft 48 fixedly secured at its lower end in a suitable manner (not shown) to one end of an elongated base member 50 which has a small reversible drive motor 52 and a speed reducer 54 mounted thereon adjacent an opposite end, for operating a cam mechanism 56.

As is shown in FIG. 8, each of the pressure plate assemblies 118-2 is movable by the cam mechanism 56 from a solid line retracted position to a dashed line position in a ventricle compressing operation. For this purpose, the cam mechanism 56 includes an essentially annular, vertically movable first camming plate 58 encircling the central support hub 46 and mounted with eight radially extending arms 60, each having a tapered camming surface 62. In the disclosed embodiment, six of the camming surfaces 62 engage respective camming rollers 64 on respective ones of the pressure plates 120-2 of the pressure plate assemblies 118-2 so that vertical movement of the camming plate 58 moves the pressure plate assemblies to their ventricle compressing positions. Located between selected ones of the camming arms 60 are at least three (four being shown) coil springs 66, which are disposed between vertically spaced projecting upper and lower arms 68 on the support hub 46 and the camming plate 58, respectively, to produce balanced return of the cam mechanism 56 to an initial lower position. In the alternative, additional ones of the pressure plate assemblies 118-2 also may be provided on the support hub 46 for operation by the remaining two camming arms 60, to also provide additional compression of the left ventricle 12, or compression of a right ventricle, depending upon the position of the pressure plate assemblies on the heart. Vertical movement of the first camming plate 58 is accomplished by a plurality of circumferentially spaced, tapered cam segments 70 mounted on a second camming plate 72 supported for rotation on the depending shaft 48 of the support hub 46 by suitable bearings 74. An upper end of each of the tapered cam segments 70 is disposed in a correspondingly tapered groove 76 in a bottom wall of a respective one of the radially extending camming arms 60, so that rotation of the second camming plate 72 causes raising of the first camming plate 58 and movement of the pressure plate assemblies 118-2 to their broken line positions during a ventricle compression operation. As viewed in FIG. 9, the rotatable second camming plate 72 is rotated clockwise for this purpose by the reversible drive motor 52 and the speed reducer 54, through a drive shaft 78 journaled at its left-hand end in a bearing 80 on the base member 50 and having a pinion gear 82 engaged with a radially outward extending toothed segment 84 of the rotatable second camming plate 72. Similarly, the rotatable camming plate 72 is rotated in a reverse direction (counter clockwise in FIG. 9) to permit the downward movement of the vertically movable first camming plate 58, and thus movement of the pressure plate assemblies 118-2 back to their solid line positions, during a ventricle filling operation.

Figure 10:
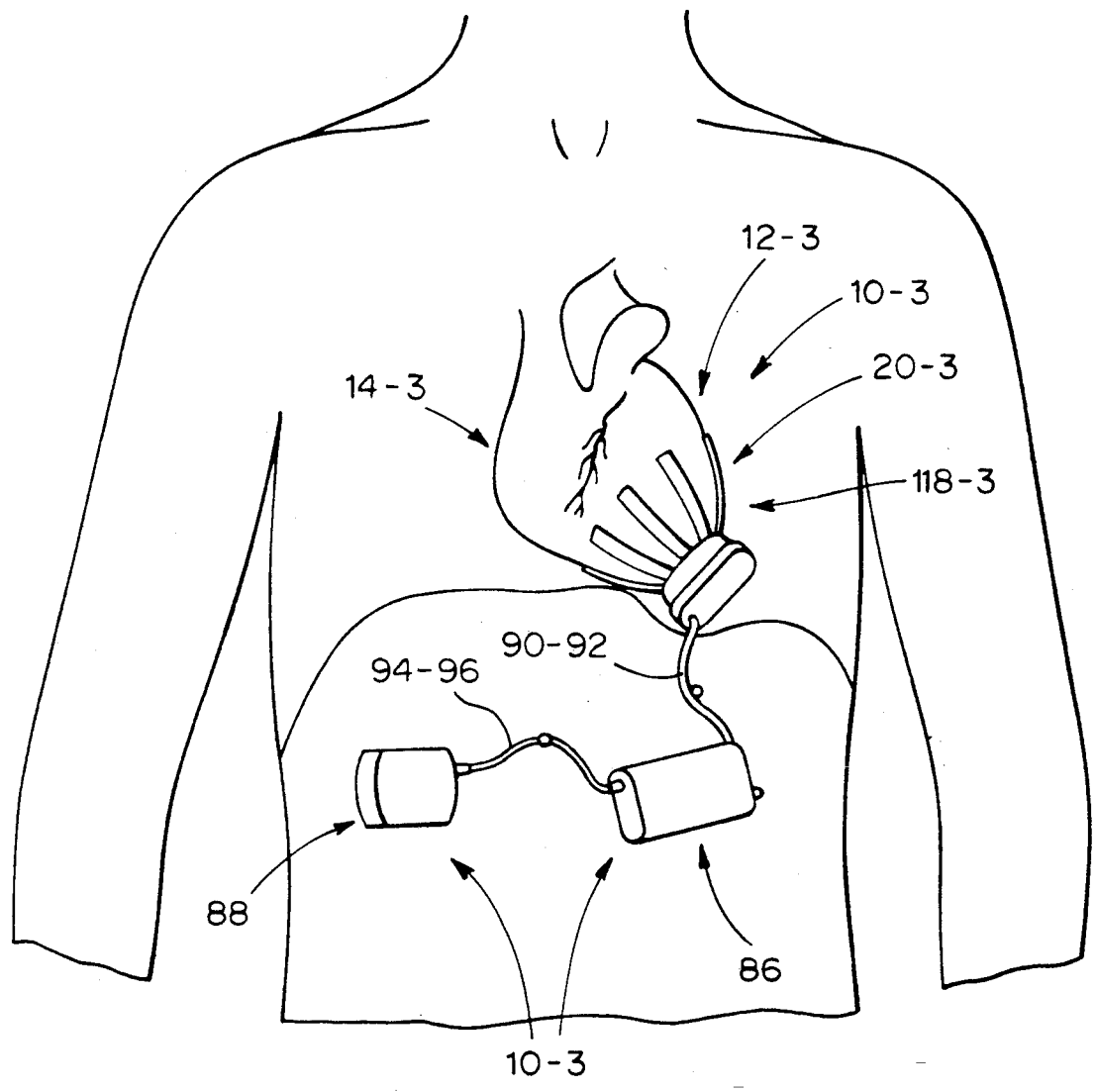
FIG. 10 is a schematic diagram of a ventricular assist device comprising a third embodiment of a direct cardiac pumping mechanism in accordance with the invention, shown implanted in a patient's body.

FIGS. 10-15 illustrate a third embodiment of the invention in which a biocompatible ventricular assist device 10-3 comprises a pumping or compression mechanism 20-3 which includes eight pressure plate or compression assemblies 118-3 (all shown only in FIGS. 12 and 13) and an electrical-to-fluid energy converter 86 operated from an electronic control module 88 comprising an electrical power source and control circuitry, neither of which is shown. The pumping mechanism 20-3 is positionable on a left ventricle 12-3 of a heart 14-3 as illustrated in FIG. 10 and is connected to the energy converter 86 by a pressurized hydraulic fluid hose 90 and a low compliance fluid hose 92, shown generally in FIG. 10 and more specifically in FIGS. 14 and 15. The energy converter 86 is connected to the electronic control module 88 by a cable 94 formed of electrical wires 96, as illustrated generally in FIG. 10.

Referring to FIGS. 11, 12 and 13, the eight pressure plate assemblies 118-3 include respective pressure plates or fingers 120-3 which surround the left heart ventricle 12-3 and which are provided with gel-filled compression pads 22-3. Lower ends of the pressure plates 120-3 are pivotally mounted by pivot pins 130-3 (FIG. 11) on a central support member, in this instance a horizontally disposed, circular support plate 46-3 fixedly secured to upper ends of vertically extending support posts 100 having lower ends fixedly secured to a horizontally disposed base plate 102. Preferably, as viewed in FIG. 11, the pressure plate assemblies 118-3 which are disposed around the exterior of the heart left ventricle 12-3 are longer than the pressure plate assemblies on the opposite side of the heart 14-3 adjacent a heart right ventricle. In this regard, the left-hand pressure plates 120-3, as viewed in FIG. 11, may be of two-part construction, comprising an inner base portion 120-3a and an outer portion 120-2b secured together by suitable connectors, e.g.; small bolts, screws or rivets, for "customizing" the length of these plates to the size of the heart involved.

The base plate 102 forms respective lower ends of a pair of metal bellows 104 having upper ends defined by a movable top plate 106, with the base plate and top plate being interconnected by expandable-and-contractible metal bellows portions 108 having opposite ends welded to the base plate and the top plate, respectively. The bellows top plate 106 has a plurality of upstanding pressure plate operating members 110 having lower ends fixed to the top plate, with their upper ends provided with camming rollers 134-3 engageable with respective ones of the pressure plates 120-3. Thus, as fluid is introduced into the lower ends of the two bellows 104 from the energy converter 86 (FIG. 10) via the pressurized hydraulic hose 90 and suitable internal conduits (not shown), both bellows expand and cause the top plate 106, and thus the operating members 110 and the camming rollers 134-3, to move upward to move the pressure plate assemblies 118-3 from their solid line positions to ventricle compressing dashed line positions, as shown in FIG. 11. Similarly, when hydraulic pressure on the bellows 104 is removed, the pressure plate assemblies 118-3 can return to their solid line positions to permit expansion of the heart ventricle 12-3. The use of the two bellows 104, rather than a single bellows, is advantageous because the resulting physical package fits better anatomically around the heart 14-3 and does not interfere with the patient's chest wall.

Figure 14:
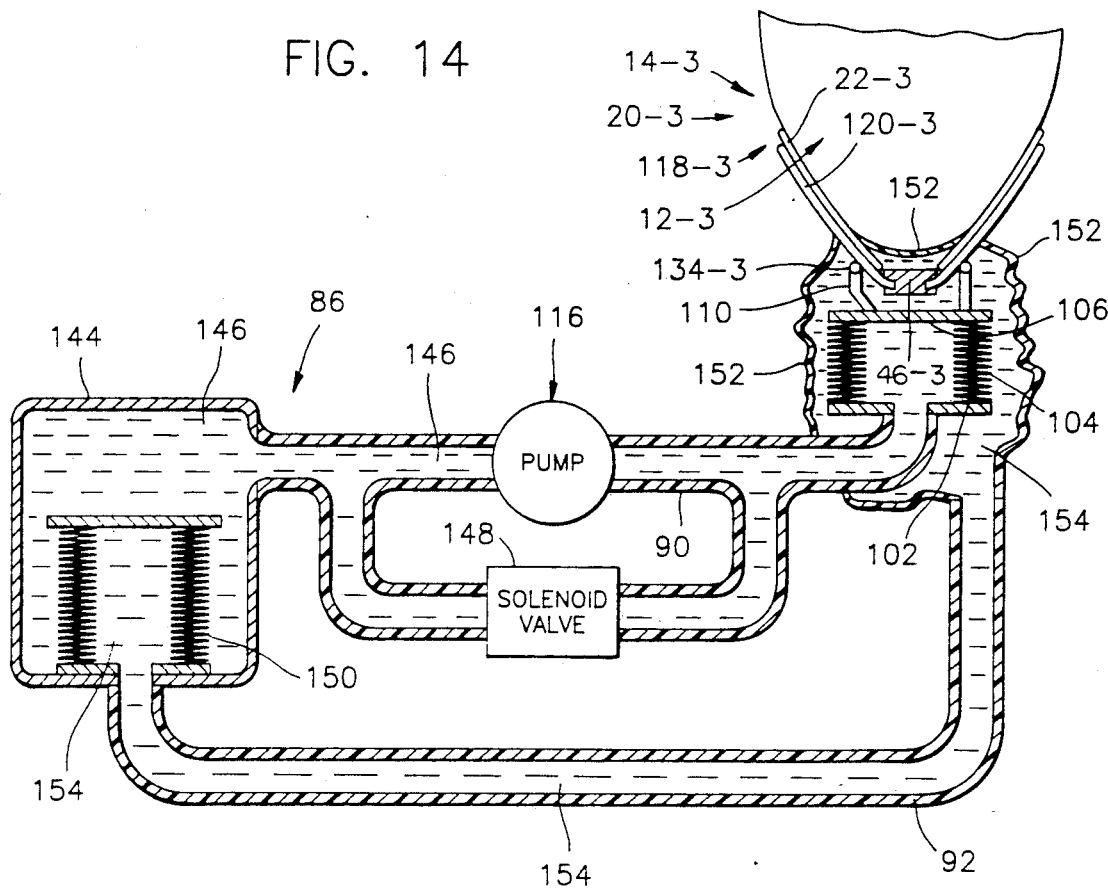
FIG. 14 is a schematic diagram of the pumping mechanism shown in FIG. 10.
Figure 15:
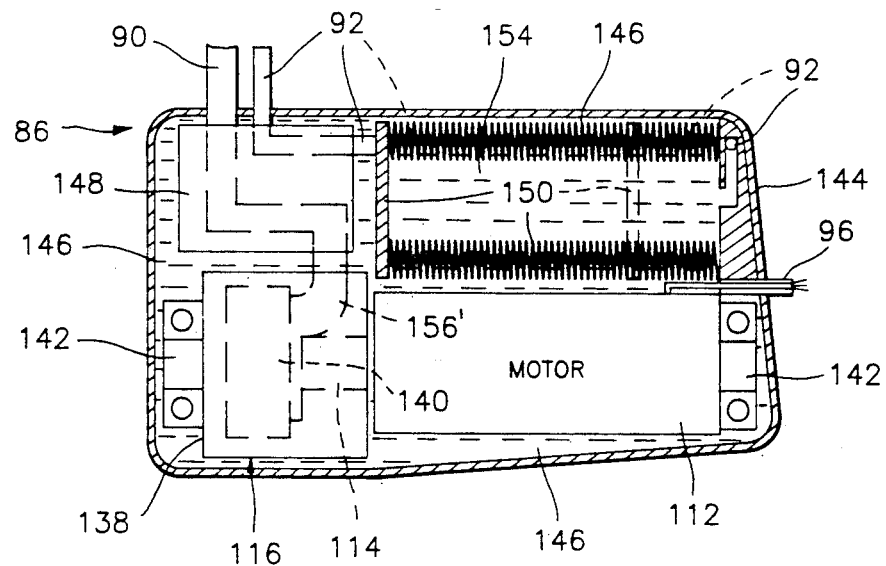
FIG. 15 is a cross-sectional view of a generator-type energy converter of the pumping mechanism shown in FIG. 10.
Figure 17:
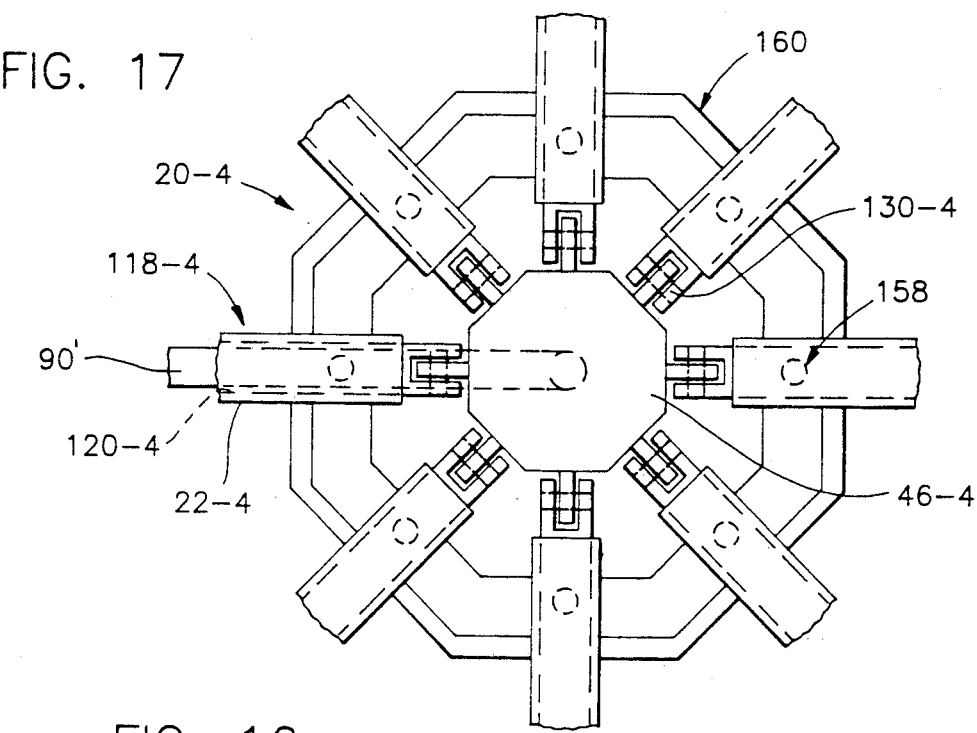
FIG. 17 is a top view as seen along the line 17—17 in FIG. 16.

Referring to FIGS. 14 and 15, the energy converter 86 converts electrical energy into pressurized hydraulic fluid energy, to operate the pumping mechanism 20-3. For this purpose the energy converter 86 includes a small reversible, brushless DC servomotor 112 (FIG. 15). A drive shaft 114 of the motor 112 operates a gerotor pump 116, with the drive shaft extending through an opening in a pump housing 138 and having an impeller 140 of the pump fixed on an outer end of the shaft within the housing. Opposite ends of the drive shaft 114 are supported in bearings 142 fixedly mounted to a wall of a sealed metal casing 144 filled with a hydraulic fluid 146. Power for the drive motor 112 is provided by a plurality of the wires 96, which extend through an opening in an end wall of the sealed casing 144 from the electronic control module 88. The energy converter 86 further comprises a normally closed electrical solenoid valve 148 of low power design connected in parallel with the pump, as illustrated in FIG. 14, and a welded metal compliance bellows 150 disposed within the hydraulic fluid 146 in the sealed casing 144 and movable between an expanded solid line position and a compressed dashed line position, as shown in FIG. 15. For this purpose, the low compliance hose 92, which is connected to the left-hand end of the sealed casing 144, as viewed in FIG. 15, extends to the right adjacent the bellows 150 and is connected to a fixed right-hand end thereof, as viewed in this figure.

As is illustrated in FIG. 14, the lower portion of the pumping mechanism 20-3 is enclosed within a covering or casing 152 of a flexible fluid-impervious material, such as polyurethane elastomer, suitably sealed or bonded to the associated parts of the pumping mechanism to define a leakproof container. As is shown in FIG. 14, the interior of the covering 152 and the interior of the metal bellows 150 in the energy converter casing 144 are filled with a hydraulic fluid 154 to define a closed fluid system.

In operation, during systole (ventricle compression) the servomotor 112 and the spring-loaded solenoid valve 148 are energized from an electrical power source (not shown) in the electronic control module 88 to drive the gerotor pump 116 and close the solenoid valve 148, respectively, causing four events to occur simultaneously. First, the gerotor pump 116 draws in fluid 146 from within the sealed casing 144 and pressurizes the fluid. Second, the gerotor pump 116 also ejects the pressurized fluid 146 through a fluid passage 156 with sufficient pressure so that the fluid flows through the pressurized fluid hose 90 into the bellows 104 of the pumping mechanism 20-3, causing the bellows to expand and move the pressure plate assemblies 118-3 into compressing relationship with the left heart ventricle 12-3. Third, as the pressure in the sealed casing 144 begins to drop because the gerotor pump 116 is removing fluid, the compliance bellows 150 in the sealed casing expands from a dashed line position to a solid line position in FIG. 15, to prevent a vacuum from being formed in the sealed casing. Fourth, fluid in the interior of the sealed covering 152 which is displaced by expansion of the pumping mechanism bellows 104 will flow through the compliance hose 92 into the interior of the compliance bellows 150. Conversely, during diastole (ventricle filling), when the direction of rotation of the servomotor 112 is reversed, the direction of fluid flow is reversed, ejecting the hydraulic fluid in the pumping mechanism bellows 104 back into the sealed casing 144. Similarly, if the gerotor pump 116, or the electrical power source or other electronic circuitry (neither shown) in the electronic control module 88 should fail, the normally closed solenoid valve 148 will automatically open with fluid flow being reversed and bypassing the pump 116 in essentially the same manner so that the pressure plate assemblies 118-3 automatically are decoupled from the heart 14-4.

FIGS. 16-20 disclose a fourth embodiment of the invention in which a ventricular assist device 10-4 comprises a pumping or compression mechanism 20-4 also having eight pressure plate or compression assemblies 118-4, each including a compression plate 120-4 in the form of an elongated "finger" or "paddle", which encompass a heart 14-4. As in the embodiments of the invention shown in FIGS. 8-15, lower ends of the compression plates 120-4 are pivotally mounted on a central support member, in this instance an octagonal mounting hub 46-4, by pivot pins 130-4. To minimize wear, a hard surface coating, such as a diamond film (not shown), produced by ion-implantation and/or chemical vapor deposition, may be applied to pivot surfaces of both the pressure plates 120-4 and the pivot pins 130-4.

The pumping mechanism 20-4 uses a miniature hydraulic actuator 158 to pivot each pressure plate assembly 118-4 inward. The hydraulic actuators 158 are integrally formed as parts of a hydraulic fluid manifold 160, also of octagonal construction, and connected to a suitable hydraulic fluid supply 144' via a pump 116' and a pressurized fluid hose 90'. Each actuator 158 includes a cylinder 162 having a cylinder wall 162w formed in a peripheral portion 164 of the manifold in fluid communication with an interior of the manifold, and a miniature piston 166 (e.g., on the order of 0.187 inch in diameter) disposed for reciprocating movement in the cylinder wall. An outer end of each piston 166 is adapted to slidably engage its associated compression plate 120-4 for pivoting the compression plate inward in a ventricle compressing operation, but is otherwise disconnected from the compression plate, to provide a "decoupling" feature to the pumping mechanism 20-4, by allowing the pressure plate assemblies 118-4 to float freely with the heart 14-4 when the pistons are stationary.

Figure 16:
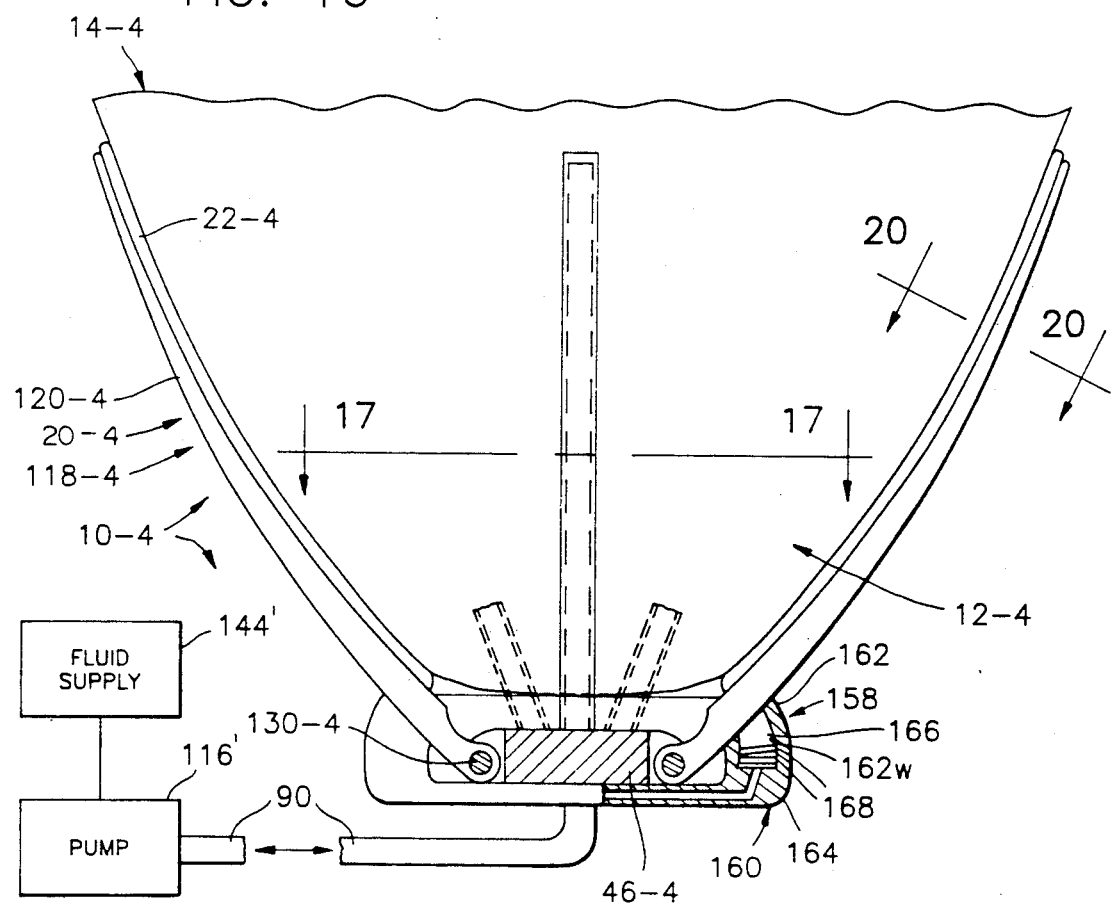
FIG. 16 is a front elevational view, partially in cross-section and with certain parts omitted, of a fourth embodiment of a direct cardiac pumping mechanism in accordance with the invention.
Figure 18:
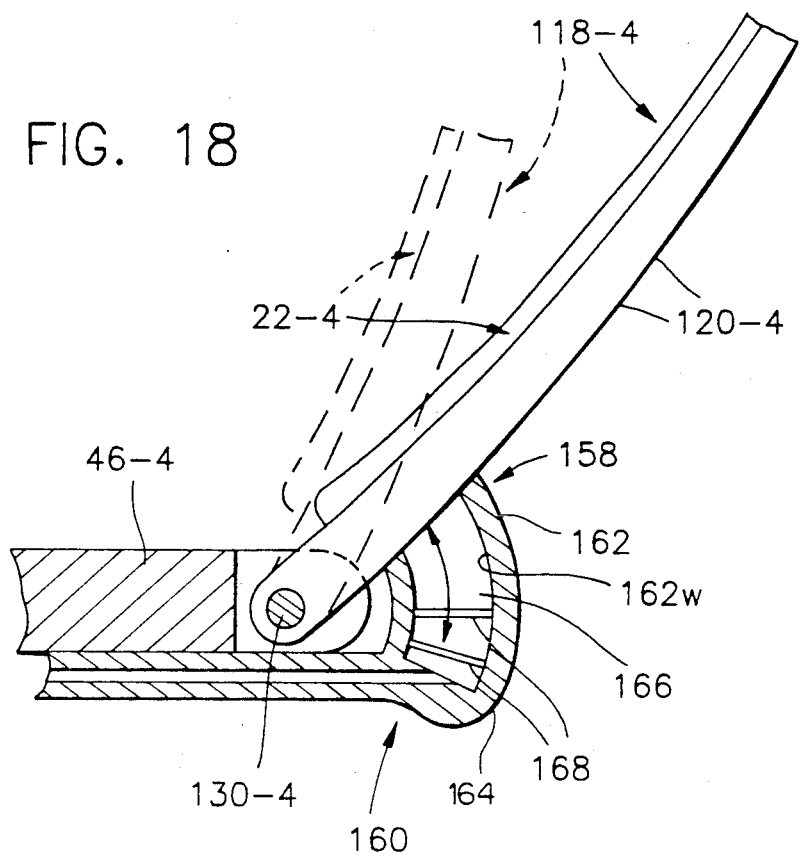
FIG. 18 is an enlarged cross-sectional view of a portion of the pumping mechanism shown in FIG. 16.
Figure 19:
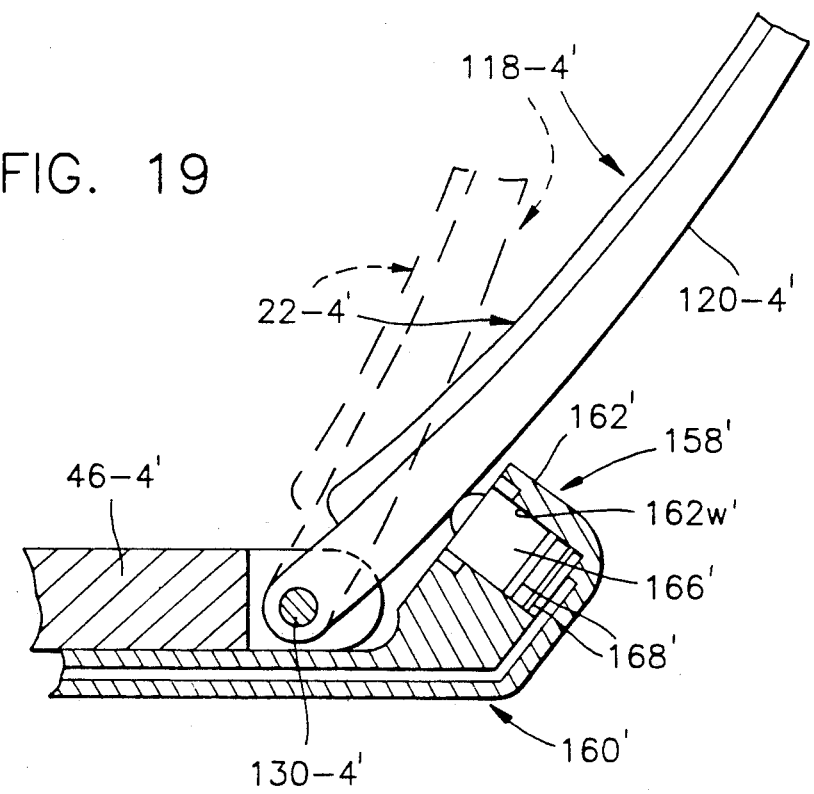
FIG. 19 is a cross-sectional view similar to FIG. 18, showing an alternate arrangement.

In order to minimize the number of components and the overall size of the pumping mechanism 20-4, referring to Figures 16 and 18, each piston 166, which has a circular cross section, may be in the form of a partial toroid with a curvature along a circumferentially extending axis and having, by way of example, a radius on the order of 0.400 inch. Similarly, the associated cylinder wall 162w is of the same arcuate configuration, with the piston 166 mounted for sliding movement in the cylinder wall along an arcuate path, with the shape of the cylinder wall precisely matching that of the piston. To prevent wear, a titanium alloy, having a hard surface coating, also may be used to form the cylinder wall 162w. In the alternative to the actuator 158 having the arcuate cylinder wall-piston arrangement 162w, 166 shown in FIGS. 16 and 18, an actuator 158' having a cylinder 162' with a cylinder wall 162w' and a piston 166' arranged in a conventional straight-line arrangement as shown in FIG. 19, may be used, with this arrangement requiring that a manifold 160' be slightly larger than the manifold 160 shown in FIGS. 16 and 18.

Regardless of whether the arcuate actuator 158 or the straight-line actuator 158' is used, referring to FIGS. 16 and 18, by way of example, sealing of the hydraulic fluid against flow around the piston 166 may be accomplished by one or more miniature metallic rings 168 secured to the piston by being disposed in a respective small annular groove in the piston, such as in an automobile engine. For this purpose, the cross-section of the cylinder wall 162w must be perfectly circular at all points, to provide uniform contact between the metallic ring(s) 168 and the cylinder wall. In the alternative, an elastomeric piston seal (not shown) may be used in place of the metallic ring 168, as for example, a seal made of a composite material having a TEFLON (polytetraflouroethylene) base.

Figure 20:
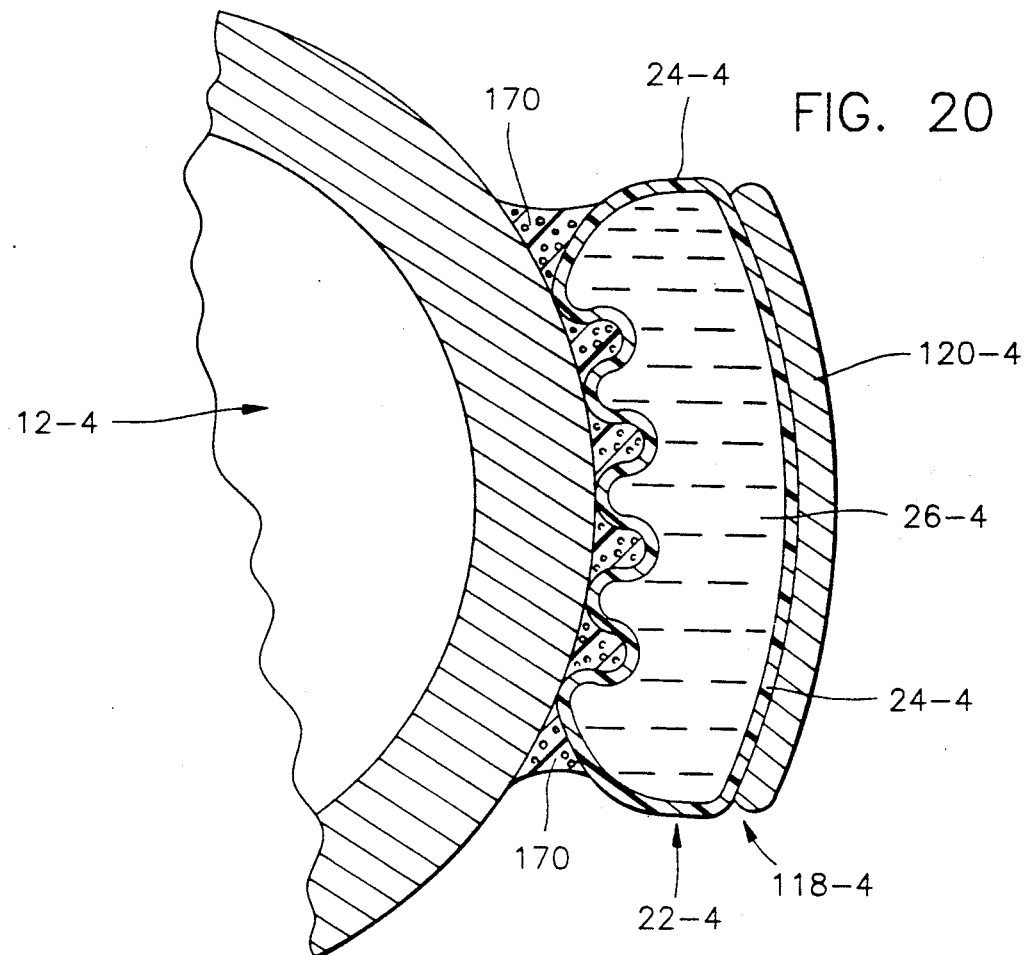
FIG. 20 is an enlarged cross-sectional view taken along the line 20—20 in FIG. 16.

Referring to FIG. 20, as in the previous embodiments of the invention, each of the pressure plate assemblies 118-4 comprises a gel-filled contact pad 22-4 mounted on a pressure plate or finger 120-4. In this instance, however, a heart ventricle engaging surface of the contact pad 22-4 is provided with a layer of a soft, open-cell urethane foam 170 for making direct contact with the surface of a heart ventricle 12-4. The open structure of the urethane foam 170 also promotes the ingrowth of heart ventricle tissue to the contact pad 22-4, which includes a sheath 24-4 formed of a bio-compatible urethane elastomer, while the inside of the pad is filled with a soft elastomer gel 26-4. An inner support surface of the contact pad 22-4, which is suitably bonded to an inner surface of the pressure plate 120-4, is of smooth construction, while the surface of the pad adjacent the heart ventricle 12-4 and having the layer of urethane foam 170 thereon, is of a convoluted construction (corrugations or dimples) to allow the pad to easily shrink and expand as the size of the heart ventricle 12-4 changes. At the same time, the layer of urethane foam 170 which fills the spaces between the convolutions of the convoluted surface also shrinks and expands without interfering with the shrinkage and expansion of the heart surface.

Figure 21:
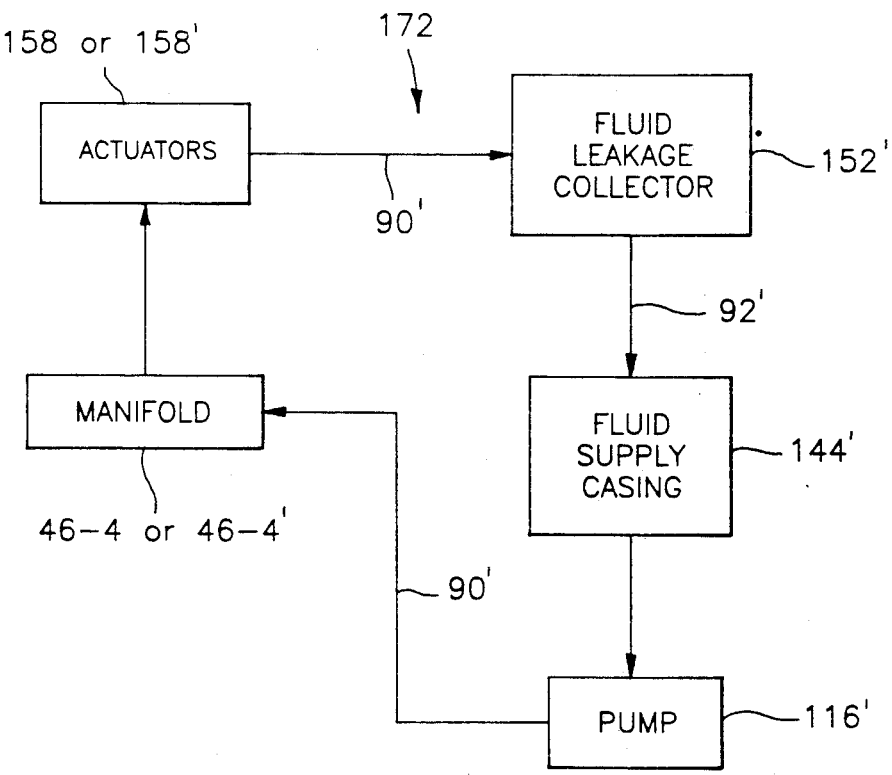
FIG. 21 is a block diagram of a closed loop fluid recovery system which may be used in the embodiment of the invention shown in FIGS. 16-20.

FIG. 21 illustrates diagrammatically a closed loop system 172 for collecting and reusing hydraulic fluid which may leak from the hydraulic actuators 158 or 158' past the metallic rings (or elastomer seals) 168 or 168 of the pistons 166 or 166'. The system 172 comprises a fluid leakage collector, which may be, for example, in the form of a covering or casing 152, for the lower portion of the pumping mechanism 20-4, such as the covering 152 in the embodiment of the invention shown in FIGS. 10-15. The collector 152' captures any hydraulic fluid which may leak from the actuators 158 or 158', with the fluid draining back through a compliance hose 92' to a fluid supply casing 144' containing a pump 116', for operating the actuators 158 or 158' through a pressurized hydraulic fluid hose 90, and the manifolds 46-4 or 46-4', respectively.

Figure 22:
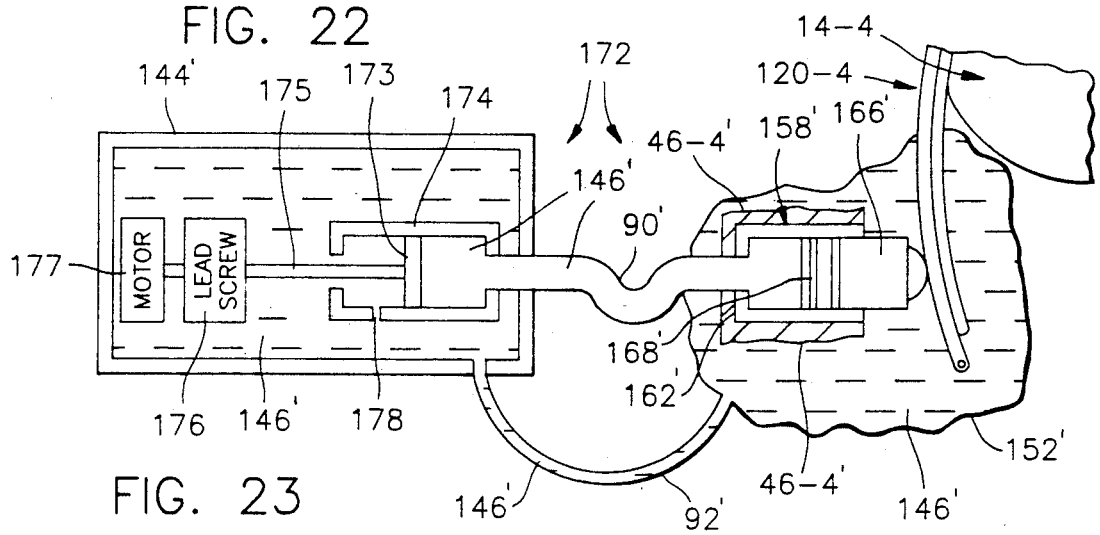

More specifically, FIG. 22 is a schematic view illustrating the closed loop fluid recovery system 172 in conjunction with one of the miniature actuators 158'. In the embodiment shown the pump 116' is in the form of a piston 173 disposed in a cylinder 174 and having a connecting rod 175 reciprocated by a lead screw 176 driven by a small reversible motor 177. This entire assembly is located in the fluid supply sealed casing 144', which is filled with hydraulic fluid 146', and the cylinder 174 includes a small intake opening 178 in a side wall thereof. The cylinder 174 also is connected by the pressurized hydraulic line 90' to the manifold 46-4', and thus to each of the actuators 158', with the manifold and the actuators being encased, along with lower portions of the compression plate assemblies 120-4, in the sealed covering 152', which is connected to the fluid supply casing 144' by the compliance hydraulic line 92'. Thus, when one of the actuators 158, leaks fluid 146', the fluid merely escapes from the high pressure cylinder 162' of the actuator into the lower pressure covering 152', and flows back to the fluid supply casing 144', without any fluid being lost from the system 172.

Figure 23:
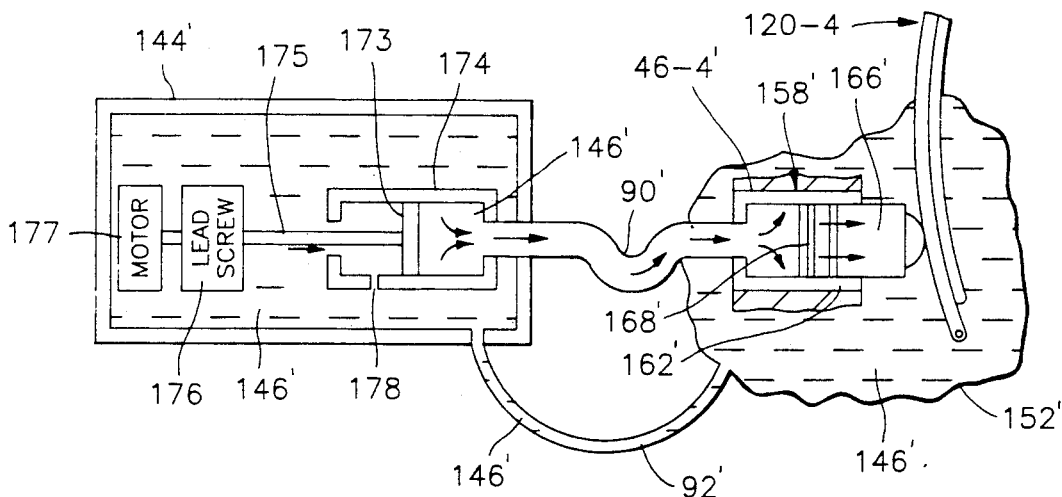
Figure 24:
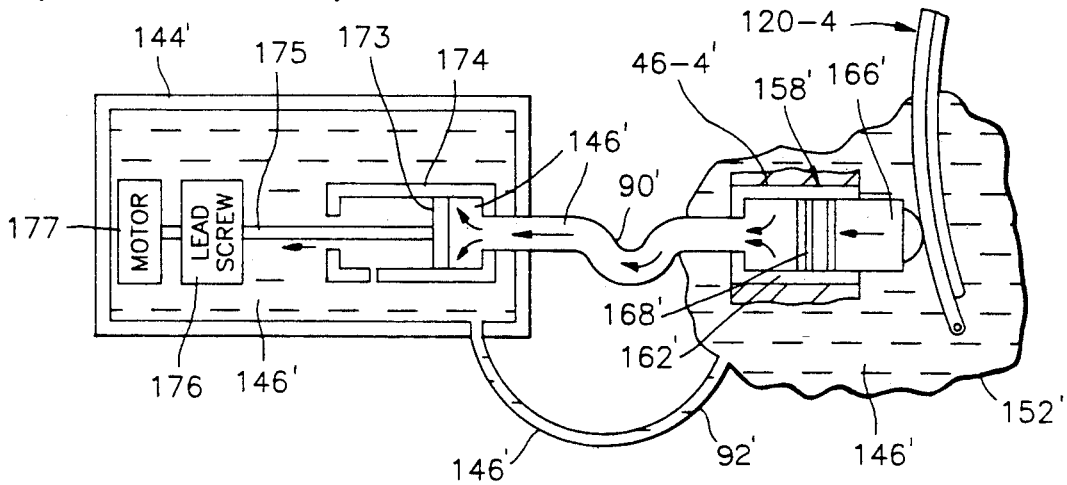

With reference to FIG. 23, in normal operation, during systole (ventricular compression) the piston 173 is advanced by the lead screw 176 and the motor 177, as indicated by the arrows, to cause the operation of the pistons 166' of the actuators 158' and pivoting of the compression plate assemblies 120-4 against the heart 14-4. Referring to FIG. 24, after systole, the motor 177 reverses direction to retract the piston 173, causing fluid flow in the pressurized hydraulic fluid line 90' in a reverse direction, and retraction of the pistons 166' of the miniature actuators 158', as illustrated by the arrows in this figure. Then, if no leakage from any of the miniature actuators 158' has occurred, the pistons 166' in the actuators and the piston 173 in the fluid supply sealed container 144' will engage the bottoms or left-hand ends of their respective cylinders 162' and 174 simultaneously, as shown in FIG. 25.

On the other hand, with reference to FIG. 26, if hydraulic fluid 146' has leaked from one of the miniature actuators 158', thus reducing the volume of hydraulic fluid in the system 172 between the piston 166' of the miniature actuator 158' and the actuator operating piston 173 in the fluid supply sealed container 144', the piston 166' will engage the bottom of its associated cylinder 162' before the motor 177' has stopped. Referring to FIG. 27, as the motor 177 then continues to operate and cause further retraction of the piston 173, a vacuum is created inside its cylinder 174. Then, when the piston 173 has been retracted so as to uncover the small hole 178 in the side wall of the cylinder 174, additional hydraulic fluid 146' is sucked into the interior of the cylinder, with the piston eventually engaging and stopping against the bottom or left-hand end of the cylinder, as viewed in FIG. 27. As a result, no hydraulic fluid 146' is lost from the system 172 as a result of leakage from the actuators 158', and the system continues to operate in its normal manner.

In summary, various improvements in a cardiac ventricular assist device, including a new and improved cardiac compression gel-filled contact pad 22, have been disclosed. For example, with reference to FIGS. 1-7, the gel-filled contact pad 22 is mounted on a pressure plate 120 of a cardiac compression assembly 20, for engaging an outer surface of at least one heart ventricle, such as the left ventricle 12, with the outer periphery of the gel-filled contact pad extending outward beyond the outer periphery of the pressure plate to preclude damage to the ventricle, particularly by the peripheral edges of the pressure plate. The gel-filled contact pad 22 has a generally concave configuration so as to be adapted to conform uniformly to the left ventricle 12, so that applied force by the pad is distributed uniformly over the ventricle's surface. The contact pad sheath 24 has an undulating surface on its opposite sides, formed by the raised dimples 28, to facilitate shrinkage and expansion of the contact pad with the left ventricle 12, so that the ventricle can shrink and expand naturally, without undue strain and without being damaged. The raised dimples 28 also facilitate securing of the contact pad to the pressure plate 120 and the left ventricle 12. In this regard, selected ones of the raised dimples 28 (or the peaks of the corrugations in FIG. 20) may be glued to the left ventricle 12, and other ones of the dimples may be provided with the tissue growth-producing islands 34, for securing the contact pad to the ventricle. The gel-filled contact pad 11 indicated in FIG. 20 also may include the tissue growth-promoting porous urethane elastomer foam 170. The gel-filled contact pad 22 also may readily be sutured to the left ventricle 12 by the integrally formed suturing tabs 36. In addition, the raised dimples 28 form depressed portions or valleys 42 for receiving the grid-type, wire mesh electrode 38, for transmitting heart signals from the left ventricle 12, and/or applying control signals, such as cardioverting-/defibrillating pulses, to the ventricle. Other improved forms of the cardiac ventricular assist device 10, including various improved pumping or compression mechanisms 20, also have been disclosed in FIGS. 8-21.

It is intended that all matter contained in the above description and shown in the accompanying drawings be interpreted not in any limiting sense, but as demonstrative. It is also to be understood that the following claims are intended to cover all of the generic and specific features of the invention.

We claim:

1. A ventricular assist device which can be implanted in a patient user exterior to the heart and which comprises:
    a pumping means which includes one or more movable ventricle compression assemblies;
    gel-filled pad means forming respective parts of the one or more movable ventricle compression assemblies, said gel-filled pad means being adapted for engaging an outer surface of at least one heart ventricle; and
    operating means for cyclically actuating the one or more ventricle compression assemblies, such that the ventricle is, first, compressed to aid blood ejection therefrom, and second, released to permit refilling.

2. The ventricular assist device as recited in claim 1, in which each of the gel-filled pad means has a generally concave configuration so as to be adapted to conform to the heart ventricle.

3. The ventricular assist device as recited in claim 1, in which each ventricle compression assembly includes a pivotable pressure plate connected to the operating means and having an outer periphery, each of the gel-filled pad means being mounted on a respective one of the plates and extending beyond the outer periphery of the plate.

4. The ventricular assist device as recited in claim 1, in which each of the gel-filled pad means includes means which is adapted for gluing and/or suturing the respective compression assembly to the heart ventricle.

5. The ventricular assist device as recited in claim 1, in which each of the gel-filled pad means includes a hollow sheath formed of soft, electrically insulating material.

6. The ventricular assist device as recited in claim 5, in which the soft, electrically insulating material of the sheath has a specific gravity and stiffness similar to that of human muscle tissue so as to be adapted to be easily deformed.

7. The ventricular assist device as recited in claim 6, in which the material of the sheath is a polyurethane elastomer.

8. The ventricular assist device as recited in claim 1, in which each of the gel-filled pad means is filled with a soft gel having the characteristics of polyurethane or silicone.

9. The ventricular assist device as recited in claim 1, in which each of the gel-filled pad means has an undulating surface formed by a series of multiple raised portions adapted to engage the heart ventricle so as to shrink and expand with the ventricle.

10. The ventricular assist device as recited in claim 9, in which the raised portions of the undulating surface are intersecting rows of raised dimples.

11. The ventricular assist device as recited in claim 10, in which at least one of the gel-filled pad means includes electrode means for transmitting signals from the heart ventricle and/or applying signals to the heart ventricle.

12. The ventricular assist device as recited in claim 11, in which the electrode means is mounted in depressed portions of the undulating surface of the at least one gel-filled pad means between selected ones of the raised dimples.

13. The ventricular assist device as recited in claim 12, in which the electrode means is in the form of a grid having intersecting strip portions which define dimple-receiving openings therebetween.

14. The ventricular assist device as recited in claim 9, in which selected ones of the raised portions include surface portion means adapted to promote ventricle tissue growth to the gel-filled pad means.

15. The ventricular assist device as recited in claim 14, in which the tissue growth-promoting surface portion means are formed of DACRON (polyester).

16. The ventricular assist device as recited in claim 1, in which each of the gel-filled pad means has opposite sides each having an undulating surface formed by a series of multiple raised portions.

17. The ventricular assist device as recited in claim 16, in which each of the raised portions of the undulating surfaces are intersecting rows of raised dimples, with selected ones of the dimples on one side of the gel-filled pad means being bonded to a respective one of the pressure plates and selected ones of the dimples on the other side of the gel-filled pad means being adapted to be bonded to the heart ventricle.

18. The ventricular assist device as recited in claim 1, in which at least one of the gel-filled pad means includes electrode means for transmitting signals from the heart ventricle and/or applying signals to the heart ventricle.

19. The ventricular assist device as recited in claim 18, in which the electrode means is formed of a titanium wire mesh.

20. The ventricular assist device as recited in claim 1, in which each of the gel-filled pad means includes surface portion means for promoting ventricle tissue growth to the gel-filled pad means.

21. The ventricular assist device as recited in claim 20, in which the surface portion means for promoting tissue growth are formed of DACRON (polyester).

22. A cardiac compression assembly which is intended for use in a cardiac assist device and which includes:
a movable pressure plate;
gel-filled pad means mounted on the pressure plate and being adapted for engaging an outer surface of at least one heart ventricle; and
mounting means for mounting the cardiac compression assembly in a cardiac assist device.

23. The cardiac compression assembly as recited in claim 22, in which the gel-filled pad means has a generally concave configuration so as to be adapted to conform to the heart ventricle.

24. The cardiac compression assembly as recited in claim 22, in which the pressure plate has an outer periphery, and the gel-filled pad means on the pressure plate extends beyond the outer periphery of the plate.

25. The cardiac compression assembly as recited in claim 22, in which the gel-filled pad means includes means which is adapted for gluing and/or suturing the cardiac compression assembly to the heart ventricle.

26. The cardiac compression assembly as recited in claim 22, in which the gel-filled pad includes a hollow sheath formed of soft, electrically insulating material.

27. The cardiac compression assembly as recited in claim 26, in which the soft, electrically insulating material of the sheath has a specific gravity and stiffness similar to that of human muscle tissue so as to be adapted to be easily deformed.

28. The cardiac compression assembly as recited in claim 27, in which the material of the sheath is a polyurethane elastomer.

29. The cardiac compression assembly as recited in claim 22, in which the gel-filled pad means is filled with a soft gel having the characteristics of polyurethane or silicone.

30. The cardiac compression assembly as recited in claim 22, in which the gel-filled pad means has an undulating surface formed of a series of multiple raised portions and adapted to engage the heart ventricle so as to shrink and expand with the ventricle.

31. The cardiac compression assembly as recited in claim 30, in which selected ones of the raised portions include surface portion means adapted to promote ventricle tissue growth to the gel-filled pad means.

32. The cardiac compression assembly as recited in claim 31, in which the tissue growth-promoting surface portion means is formed of DACRON (polyester).

33. The cardiac compression assembly as recited in claim 32, in which the raised portions of the undulating surface are intersecting rows of raised dimples.

34. The cardiac compression assembly as recited in claim 33, in which the gel-filled pad means includes electrode means for transmitting signals from the heart ventricle and/or applying signals to the heart ventricle.

35. The cardiac compression assembly as recited in claim 34, in which the electrode means is mounted in depressed portions of the undulating surface of the gel-filled pad means between selected ones of the raised dimples.

36. The cardiac compression assembly as recited in claim 35, in which the electrode means is in the form of a grid having intersecting strip portions which define dimple-receiving openings therebetween.

37. The cardiac compression assembly as recited in claim 22, in which the gel-filled pad means has opposite sides each having an undulating surface formed by a series of multiple raised portions.

38. The cardiac compression assembly as recited in claim 37, in which the raised portions of the undulating surfaces are formed by intersecting rows of dimples, with selected ones of the dimples on one side of the gel-filled pad means being bonded to the pressure plate, and selected ones of the dimples on the opposite side of the gel-filled pad means being adapted to be bonded to the heart ventricle.

39. The cardiac compression assembly as recited in claim 22, in which the gel-filled pad means includes surface portion means for promoting ventricle tissue growth to the gel-filled pad means.

40. The cardiac compression assembly as recited in claim 39, in which the surface portion means for promoting tissue growth are formed of DACRON (polyester).

41. A cardiac compression assembly which is intended for use in a cardiac assist device and which includes:
a movable pressure plate;
flexible pad means mounted on the pressure plate and being adapted for engaging an outer surface of at least one heart ventricle, the flexible pad means having an undulating surface on at least one side thereof formed by a series of multiple raised portions; and
mounting means for mounting the cardiac compression assembly in a cardiac assist device.

42. The cardiac compression assembly as recited in claim 41, in which selected ones of the raised portions are secured to the pressure plate.

43. The cardiac compression assembly as recited in claim 41, in which selected ones of the raised portions are adapted to be secured to the heart ventricle.

44. The cardiac compression assembly as recited in claim 41, which further comprises electrode means mounted in depressed portions of the undulating surface between selected ones of the raised portions, for transmitting signals from the heart ventricle and/or applying signals to the heart ventricle.

45. The cardiac compression assembly as recited in claim 41, in which the raised portions of the pad undulating surface are intersecting rows of raised dimples.

46. The cardiac compression assembly as recited in claim 45, which further comprises electrode means for transmitting signals from the heart ventricle and/or applying signals to the heart ventricle, the electrode means being mounted in depressed portions of the pad undulating surface between selected ones of the raised dimples and comprising a grid having intersecting strip portions which define dimple-receiving openings therebetween.

47. The cardiac compression assembly as recited in claim 41, in which an opposite side of the flexible pad means also has an undulating surface formed by a series of multiple raised portions.

48. The cardiac compression assembly as recited in claim 47, in which the raised portions of the opposite sides of the flexible pad means are intersecting rows of raised dimples.

49. The cardiac compression assembly as recited in claim 41, in which selected ones of the raised portions include surface portion means adapted to promote ventricle tissue growth to the pad means.

50. The cardiac compression assembly as recited in claim 49, in which the tissue growth-promoting surface portion means are formed of DACRON (polyester).

51. A flexible cardiac compression pad, which comprises:
a flexible hollow sheath adapted for engaging a heart ventricle and formed of a soft, electrically insulating material; and
a soft gel filling the hollow sheath.

52. The flexible cardiac compression pad as recited in claim 51, in which the sheath has a generally concave configuration so as to be adapted to conform to the heart ventricle.

53. The flexible cardiac compression pad as recited in claim 51, in which the soft electrically insulating material of the sheath has a specific gravity and stiffness similar to that of human muscle tissue so as to be adapted to be easily deformed.

54. The flexible cardiac compression pad as recited in claim 53, in which the material of the sheath is a polyurethane elastomer.

55. The flexible cardiac compression pad as recited in claim 51, in which the soft gel has the characteristics of polyurethane or silicone.

56. The flexible cardiac compression pad as recited in claim 51, in which the sheath has an undulating surface on at least one side thereof formed by a series of multiple raised portions.

57. The flexible cardiac compression pad as recited in claim 56, which further comprises electrode means mounted in depressed portions of the undulating surface between selected ones of the raised portions, for transmitting signals from the heart ventricle and/or applying signals to the heart ventricle.

58. The flexible cardiac compression pad as recited in claim 56, in which an opposite side of the flexible sheath also has an undulating surface formed by a series of multiple raised portions.

59. The flexible cardiac compression pad as recited in claim 58, in which the raised portions on the opposite sides of the flexible sheath are intersecting rows of raised dimples.

60. The flexible cardiac compression pad as recited in claim 56, in which the raised portions of the pad undulating surface are intersecting rows of raised dimples.

61. The flexible cardiac compression pad as recited in claim 60, which further comprises electrode means for transmitting signals from the heart ventricle and/or applying signals to the heart ventricle, the electrode means being mounted in depressed portions of the pad undulating surface between selected ones of the raised dimples and comprising a grid having intersecting strip portions which define dimple-receiving openings therebetween.

62. The flexible cardiac compression pad as recited in claim 51, in which one side of the sheath includes surface portion means for promoting ventricle tissue growth to the sheath.

63. The flexible cardiac compression pad as recited in claim 62, in which the tissue growth-promoting surface portion means are formed of DACRON (polyester).

64. The flexible cardiac compression pad as recited in claim 62, in which the tissue growth-promoting surface portion means are formed of a soft, open-celled urethane foam.

65. A flexible cardiac compression pad, which comprises:
a flexible body member having opposite sides; and
a series of multiple raised portions defining an undulating surface on at least one side of the body member.

66. The flexible cardiac compression pad as recited in claim 65, which further comprises electrode means disposed on the at least one side of the body member between selected ones of the raised portions.

67. The flexible cardiac compression pad as recited in claim 66, in which the raised portions are rows of intersecting raised dimples and the electrode means is in the form of a grid having intersecting strips which define dimple-receiving openings therebetween.

68. The flexible cardiac compression pad as recited in claim 65, which further comprises:
a series of multiple raised portions also defining an undulating surface on an opposite side of the body member.

69. The flexible cardiac compression pad as recited in claim 68, in which the raised portions on both sides of the body member are intersecting rows of raised dimples.

70. The flexible cardiac compression pad as recited in claim 65, which further comprises:
surface portion means on selected ones of the raised portions for promoting tissue growth between a heart ventricle and the body member.

71. The flexible cardiac compression pad as recited in claim 70, in which the tissue growth-promoting surface portion means are formed of DACRON (polyester).

72. The flexible cardiac compression pad as recited in claim 20, in which the tissue growth-promoting surface portion means are formed of a soft, open-celled urethane foam.

73. A ventricular assist device which can be implanted in a patient user exterior to the heart and which comprises:
a pumping means which includes a plurality of essentially circumferentially arranged movable ventricle compression assemblies adapted to be positioned around a heart ventricle;
a support member adapted to be positioned adjacent an apex of the heart ventricle;
means for pivotally mounting lower ends of the circumferentially arranged movable ventricle compression assemblies on the support member; and
operating means for cyclically pivoting the plurality of circumferentially arranged movable ventricle compression assemblies, such that the ventricle is, first, compressed to aid blood ejection therefrom, and second, released to permit refilling.

74. The ventricular assist device as recited in claim 73, in which the operating means includes a plurality of hydraulic fluid actuators, one for each of the ventricle compression assemblies.

75. The ventricular assist device as recited in claim 74, in which each of the actuators includes a piston disposed in a wall of a cylinder.

76. The ventricular assist device as recited in claim 75, in which each piston includes a piston sealing ring.

77. The ventricular assist device as recited in claim 75, in which each piston and cylinder is of an arcuate partial toroid construction.

78. The ventricular assist device as recited in claim 75, in which each piston and cylinder is of linear, straight-line construction.

79. The ventricular assist device as recited in claim 74, in which the operating means includes a hydraulic fluid manifold located adjacent to the ventricle compression assembly supporting means, each of the actuators including a piston and a cylinder in fluid communication with the manifold.

80. The ventricular assist device as recited in claim 79, in which the manifold and the fluid cylinders are of integral one-piece construction.

81. The ventricular assist device as recited in claim 74, in which each of the ventricle compression assemblies comprises a pressure plate and a gel-filled pad supported on the pressure plate.

82. The ventricular assist device as recited in claim 81, in which a ventricle-engaging surface of the gel-filled pad is at least partially formed of a porous foam.

83. The ventricular assist device as recited in claim 82, in which the ventricle engaging surface of the gel-filled pad is of undulating construction with spaces between undulations of the surface filled with the porous foam.

84. The ventricular assist device as recited in claim 83, in which an opposite side surface of the gel-filled pad is of smooth construction and bonded to the pressure plate.

85. A ventricular assist device which can be implanted in a patient user exterior to the heart and which comprises:
   a pumping means which includes one or more movable ventricle compression assemblies;
   gel-filled pad means forming respective parts of the one or more movable ventricle compression assemblies, said gel-filled pad means being adapted for engaging an outer surface of at least one heart ventricle; and
   operating means for cyclically actuating the one or more ventricle compression assemblies, such that the ventricle is, first, compressed to aid blood ejection therefrom, and second, released to permit refilling;
   each ventricle compression assembly including a pressure plate connected to the operating means and having an outer periphery, with each of the gel-filled pad means being mounted on a respective one of the plates and extending beyond the outer periphery of the plate; and
   the pressure plate of each of the one or more movable ventricle compression assemblies being mounted on a compressive arm via an axle/bearing mount such that the pressure plate and the gel-filled pad means are adapted to follow the natural movement of the heart ventricle.

86. A cardiac compression assembly which is intended for use in a cardiac assist device and which includes:
   a pressure plate;
   gel-filled pad means mounted on the pressure plate and being adapted for engaging an outer surface of at least one heart ventricle; and
   mounting means for mounting the cardiac compression assembly in a cardiac assist device;
   the pressure plate having an outer periphery with the gel-filled pad means on the pressure plate extending beyond the outer periphery of the plate; and
   the pressure plate being mounted on a compressive arm via an axle/bearing mount such that the pressure plate and the gel-filled pad means are adapted to follow the natural movement of the heart ventricle.

87. A ventricular assist device which can be implanted in a patient user exterior to the heart and which comprises:
   a pumping means which includes a plurality of essentially circumferentially arranged movable ventricle compression assemblies adapted to be positioned around a heart ventricle;
   means for supporting lower ends of the circumferentially arranged movable ventricle compression assemblies adjacent and around an apex of the heart ventricle; and
   operating means for cyclically actuating the plurality of circumferentially arranged movable ventricle compression assemblies, such that the ventricle is, first, compressed to aid blood ejection therefrom, and second, released to permit refilling;
   the lower ends of the ventricle compression assemblies being pivotally mounted on the supporting means and the operating means including a vertically movable camming means surrounding the supporting means for moving the ventricle compression assemblies to their ventricle compressing positions.

88. The ventricular assist device as recited in claim 87, in which the operating means includes a rotatable camming means for causing vertical movement of the vertically movable camming means.

89. The ventricular assist device as recited in claim 88, in which the operating means further includes a gear means for rotating the rotatable camming means.

90. The ventricular assist device as recited in claim 89, in which the operating means further includes a drive shaft on which the gear means is mounted, a motor and a speed reducer, the motor driving the drive shaft through the speed reducer.

91. A ventricular assist device which can be implanted in a patient user exterior to the heart and which comprises:
   a pumping means which includes at least six essentially circumferentially arranged movable ventricle compression assemblies adapted to be positioned around a heart ventricle;
   means for supporting lower ends of the circumferentially arranged movable ventricle compression assemblies adjacent and around an apex of the heart ventricle; and
   operating means for cyclically actuating the circumferentially arranged movable ventricle compression assemblies, such that the ventricle is, first, compressed to aid blood ejection therefrom, and second, released to permit refilling.

92. The ventricular assist device as recited in claim 91, which includes at least eight of the ventricle compression assemblies.

93. A ventricular assist device which can be implanted in a patient user exterior to the heart and which comprises:
   a pumping means which includes a plurality of essentially circumferentially arranged movable ventricle compression assemblies adapted to be positioned around a heart ventricle;
   means for supporting lower ends of the circumferentially arranged movable ventricle compression assemblies adjacent and around an apex of the heart ventricle; and operating means for cyclically actuating the plurality of circumferentially arranged movable ventricle compression assemblies, such that the ventricle is, first, compressed to aid blood ejection therefrom, and second, released to permit refilling;

the lower ends of the ventricle compression assemblies being pivotally mounted on the supporting means and the operating means including hydraulic fluid-operating means for actuating the ventricle compression assemblies.

94. The ventricular assist device as recited in claim 93, in which the hydraulic fluid-operated means includes a bellows.

95. The ventricular assist device as recited in claim 93, in which the operating means includes energy converting means for converting electrical energy into hydraulic fluid energy for operating the hydraulic fluid-operated means.

96. The ventricular assist device as recited in claim 95, in which the energy converting means includes a hydraulic fluid pump and an electrical motor connected to drive the pump.

97. The ventricular assist device as recited in claim 90, in which:

the energy connecting means is mounted in a sealed casing filled with a hydraulic fluid; and the hydraulic fluid pump draws hydraulic fluid from within the casing and forces the fluid to the fluid-operated means, to actuate the ventricle compression assemblies.

98. The ventricular assist device as recited in claim 97, which further includes a normally closed electrical solenoid valve which forms a parallel path around the hydraulic fluid pump, the solenoid automatically opening in response to an electrical power failure to permit hydraulic fluid in the operating means to return to the sealed casing.

99. The ventricular assist device as recited in claim 97, which further comprises:

expandable-and-contractible means in the sealed casing for expanding in response to the hydraulic pump drawing fluid from the sealed casing, to prevent formation of a vacuum in the sealed casing, the expandable-and-contractible means having an interior filled with hydraulic fluid;

flexible sealed covering means for surrounding the fluid-operated means and the lower ends of the ventricle compression assemblies, the covering means also having an interior filled with hydraulic fluid; and conduit means for connecting the interiors of the expandable-and-contractible means and the covering means, so that fluid flows therebetween upon expansion and contraction of the expandable-and-retractable means.

100. The ventricular assist device as recited in claim 99, in which the expandable-and-contractible means is a bellows.

101. A ventricular assist device which can be implanted in a patient user exterior to the heart and which comprises:

a pumping means which includes a plurality of essentially circumferentially arranged movable ventricle compression assemblies adapted to be positioned around a heart ventricle;

means for supporting lower ends of the circumferentially arranged movable ventricle compression assemblies adjacent and around an apex of the heart ventricle;

operating means for cyclically actuating the plurality of circumferentially arranged movable ventricle compression assemblies, such that the ventricle is, first, compressed to aid blood ejection therefrom, and second, released to permit refilling;

the lower ends of the ventricle compression assemblies being pivotally mounted on the supporting means and the operating means including a plurality of hydraulic fluid actuators, one for each of the ventricle compression assemblies and each including a piston disposed in a wall of a cylinder;

means for collecting hydraulic fluid which may leak from the actuators;

a hydraulic fluid supply forming part of a hydraulic fluid system for operating the actuators;

pump means for transferring hydraulic fluid from the hydraulic fluid supply to operate the actuators; and means for returning collected leakage fluid in the collecting means to the hydraulic fluid supply.

102. The ventricular assist device as recited in claim 101, in which the means for collecting leaking hydraulic fluid is a flexible sealed covering means for surrounding the actuators and the lower ends of the ventricle compression assemblies, the covering also having an interior filled with the hydraulic fluid.

103. The ventricular assist device as recited in claim 101, in which:

the hydraulic fluid collecting means, fluid supply, pump means and return means form a closed loop system;

the hydraulic fluid supply includes a sealed container;

the pump means includes a cylinder and a piston disposed in the sealed container, the piston being reciprocable in the cylinder by a reversible motor, and the cylinder being connected to the actuators and including an opening in a side wall thereof for drawing hydraulic fluid in the container into the cylinder upon retraction of the piston.

* * * * *